US007005525B2

(12) United States Patent
Dioumaev et al.

(10) Patent No.: US 7,005,525 B2
(45) Date of Patent: Feb. 28, 2006

(54) RECYCLABLE CATALYSTS METHODS OF MAKING AND USING THE SAME

(75) Inventors: Vladimir K. Dioumaev, Coram, NY (US); R. Morris Bullock, Wading River, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 241 days.

(21) Appl. No.: 10/731,378

(22) Filed: Dec. 9, 2003

(65) Prior Publication Data

US 2005/0075504 A1 Apr. 7, 2005

Related U.S. Application Data

(63) Continuation-in-part of application No. 10/320,954, filed on Dec. 17, 2002, now Pat. No. 6,737,531.

(51) Int. Cl.

| | |
|---|---|
| ***C07F 11/00*** | (2006.01) |
| ***C07F 7/04*** | (2006.01) |
| ***C07C 29/04*** | (2006.01) |
| ***B01J 31/00*** | (2006.01) |

(52) U.S. Cl. ......................... 548/101; 556/59; 556/470; 556/482; 568/809; 568/814; 568/881; 502/152; 502/155

(58) Field of Classification Search ................. 502/152, 502/155; 556/59, 470, 482; 568/809, 814, 568/881; 548/101
See application file for complete search history.

(56) References Cited

U.S. PATENT DOCUMENTS

| | | | | | |
|---|---|---|---|---|---|
| 5,504,049 | A | * | 4/1996 | Crowther et al. | 502/117 |
| 5,710,298 | A | * | 1/1998 | Grubbs et al. | 556/22 |
| 5,977,393 | A | * | 11/1999 | Grubbs et al. | 556/21 |
| 6,121,395 | A | * | 9/2000 | Turner | 526/134 |
| 6,124,509 | A | * | 9/2000 | Voges et al. | 568/881 |
| 6,737,531 | B1 | * | 5/2004 | Dioumaev et al. | 548/101 |

OTHER PUBLICATIONS

Dioumaev, et al.—"A Recyclable Catalyst that Precipitates at the End of the Reaction", Nature, vol. 424, Jul. 31, 2003, pp. 530–532.

* cited by examiner

*Primary Examiner*—Porfirio Nazario-Gonzalez
(74) *Attorney, Agent, or Firm*—Margaret C. Bogosian

(57) ABSTRACT

Organometallic complexes are provided, which include a catalyst containing a transition metal, a ligand and a component having the formula $GAr^F$. $Ar^F$ is an aromatic ring system selected from phenyl, naphthalenyl, anthracenyl, fluorenyl, or indenyl. The aromatic ring system has at least a substituent selected from fluorine, hydrogen, hydrocarbyl or fluorinated hydrocarbyl, G is substituted or unsubstituted $(CH_2)_n$ or $(CF_2)_n$, wherein n is from 1 to 30, wherein further one or more $CH_2$ or $CF_2$ groups are optionally replaced by NR, PR, $SiR_2$, BR, O or S, or R is hydrocarbyl or substituted hydrocarbyl, $GAr^F$ being covalently bonded to either said transition metal or said ligand of said catalyst, thereby rendering said cationic organometallic complex liquid. The catalyst of the organometallic complex can be $[CpM(CO)_2(NHC)L_k]^+A^-$, wherein M is an atom of molybdenum or tungsten, Cp is substituted or unsubstituted cyclopentadienyl radical represented by the formula $[C_5Q^1Q^2Q^3Q^4Q^5]$, wherein $Q^1$ to $Q^5$ are independently selected from the group consisting of H radical, $GAr^F$ $C_{1-20}$ hydrocarbyl radical, substituted hydrocarbyl radical, substituted hydrocarbyl radical substituted by $GAr^F$, halogen radical, halogen-substituted hydrocarbyl radical, —OR, —C(O)R', —$CO_2$R', —$SiR'_3$ and —NR'R'', wherein R' and R'' are independently selected from the group consisting of H radical, $C_{1-20}$ hydrocarbyl radical, halogen radical, and halogen-substituted hydrocarbyl radical, wherein said $Q^1$ to $Q^5$ radicals are optionally linked to each other to form a stable bridging group, NHC is any N-heterocyclic carbene ligand, L is either any neutral electron donor ligand, wherein k is a number from 0 to 1 or L is an anionic ligand wherein k is 2, and $A^-$ is an anion. Processes using the organometallic complexes as catalysts in catalytic reactions, such as for example, the hydrosilylation of aldehydes, ketones and esters are also provided.

30 Claims, 2 Drawing Sheets

RECYCLABLE CATALYSTS METHODS OF MAKING AND USING THE SAME

REFERENCE TO RELATED APPLICATIONS

This application is a continuation-in-part of U.S. patent application Ser. No. 10/320,954 filed on Dec. 17, 2002 now U.S. Pat. No. 6,737,531.

GOVERNMENT RIGHTS IN THE INVENTION

This invention was made with Government support under contract number DE-AC02-98CH10886, awarded by the U.S. Department of Energy. The Government has certain rights in the invention.

BACKGROUND OF THE INVENTION

The present invention relates to catalysts for the homogenous hydrogenation or hydrosilylation of carbonyl compounds. More specifically, the invention relates to processes for the hydrogenation of ketones and aldehydes using organometallic complexes of tungsten (W) and molybdenum (Mo) as catalysts or catalyst precursors. The invention also relates to processes for the hydrosilylation of ketones, aldehydes and esters using the same catalysts or catalyst precursors.

Hydrogenation reactions involve the addition of hydrogen to an organic compound whereby, for example, a ketone can be reduced to an alcohol. Prior art processes have generally required the presence of a heterogeneous catalyst with a solid phase of platinum, rhodium, palladium or nickel along with relatively high hydrogen pressure and elevated temperature.

Other hydrogenation processes currently in use employ inexpensive Mo and W metals to hydrogenate ketones under mild conditions of temperature and pressure. However, a limitation encountered with these processes is the decomposition of the catalysts, due to dissociation of a phosphine ligand.

Hydrosilylation reactions involve the addition of hydrosilane to ketones, aldehydes, or esters to form primarily alkoxysilanes. Prior art hydrosilylation processes have also required rhodium, platinum or palladium complexes as catalysts.

Thus, traditional homogeneous catalysts for hydrogenation or hydrosilylation of ketones or aldehydes use precious metals such as platinum (Pt), rhodium (Rh), iridium (Ir) or ruthenium (Ru), which are expensive and, therefore, frequently uneconomical. In contrast, the catalysts of the present invention, which use either molybdenum (Mo) or tungsten (W), are prepared with less expensive metals, and, therefore, offer economic advantages.

The present invention also relates to recyclable and recoverable homogeneous catalysts including organometallic complexes that can be used in solvent-free catalytic reactions.

Homogeneous catalysts offer many advantages over heterogeneous catalysts, but the pervasive problem of separating the reaction product from the catalyst constitutes a drawback to the utility of many homogeneous systems. There have been attempts in the prior art to facilitate recycling of homogenous catalysts. For example, Zwei, X., et al. in "Reaction—controlled phase—transfer catalysis for propylene epoxidation to propylene oxide, *Science,* 292, 1139 (2001) exploits a decrease in catalyst solubility when one reagent is consumed. A more general approach utilizing the thermoregulated miscibility of organic and fluorous (fluorinated organic) solvents with catalyst recovery in the fluorous phase is described by Horvath, I. T., in "Fluorous Biphase Chemistry", *Acc. Chem. Res.,* 31, 641–650, (1998). Other attempts in the prior art used fluorous thermomorphic catalysts, which allow reactions without fluorous solvents and even without solvent at all as described by Wende, M. et al. in "*Fluorous Catalysis under Homogeneous Conditions without Fluorous Solvents,*" *J. Chem. Soc.,* 125, 5861 (2003).

The principles of green chemistry and green engineering indicate that avoiding the use of solvents is an important way to prevent generation of waste. Furthermore, a solvent-free transformation from pure reagents to pure products potentially yields a dramatic change in the properties of the medium and provides an opportunity for attaining catalyst self-precipitation. Precipitation, in turn, helps to avoid using solvents in the subsequent separation stages, further preventing waste generation. A useful catalyst should stay at least somewhat soluble until the last molecule of the substrate is consumed. Rare instances of such retention of solubility are known among compounds with a low aptitude for crystal lattice formation. Such compounds can furnish a liquid phase—a liquid clathrate—with just a few equivalents of the solvent per equivalent of the otherwise solid component. This behavior is observed among ionic complexes with weakly coordinating counterions, where the charges are delocalized over large molecular fragments, and the crystal packing forces are weakened. However, liquid clathrates have thus far not been used to enable catalysts to remain in a liquid phase in catalytic reactions.

There is, therefore, still a need in the chemical arts for catalysts that can catalyze catalytic reactions in the absence of a solvent. There is also a need for catalysts that can catalyze catalytic reactions in the liquid phase and can be easily separated from products.

SUMMARY OF THE INVENTION

The present invention relates to catalysts and processes that use catalysts for the homogeneous catalytic hydrogenation of ketones and aldehydes to alcohols with $H_2$ as the stoichiometric redundant and organometallic tungsten (W) and molybdenum (Mo) complexes as the catalysts.

The present invention also relates to catalysts and processes for the hydrosilylation of ketones, aldehydes or esters, represented by the formulas $R(C{=}O)R^1$, $R(C{=}O)H$ or $R(CO_2)R^1$. The functional groups R and $R^1$ are selected from hydrogen, $C_{1-30}$ hydrocarbyl radicals and substituted-hydrocarbyl radicals, which can be the same or different.

The catalyst or catalyst precursor includes an organometallic complex represented by the formula I $$[CpM(CO)_2(NHC)L_k]^+A^- \qquad \text{I}$$

wherein M is a molybdenum or tungsten atom; Cp is substituted or unsubstituted cyclopentadienyl radical represented by the formula $[C_5Q^1Q^2Q^3Q^4Q^5]$, wherein $Q^1$ to $Q^5$ are independently selected from the group consisting of H radicals, hydrocarbyl radicals and substituted hydrocarbyl radicals, halogens (F, Cl, Br, I), halogen-substituted hydrocarbyl radicals, and radicals represented by the formulas —OR', —C(O)R', —$CO_2$R', —$SiR'_3$, —NR'R" wherein R' and R" are independently selected from the group consisting of H radicals, hydrocarbyl radicals, halogens, and halogen-substituted hydrocarbyl radicals, wherein further $Q^1$ to $Q^5$ radicals can be optionally linked to each other to form a stable bridging group; NHC is any N-heterocyclic carbene ligand, L is either any neutral electron donor ligand wherein k is a number from 0 to 1 or L is an anionic ligand wherein k is 2, and $A^-$ is an anion.

In an embodiment, the catalysts of the invention can be prepared by reacting a metal hydride represented by the formula II:

$$CpM(CO)_2(NHC)H \qquad II$$

with a hydride removing agent selected from $BR_3$ or a compound represented by formula $Y^+A^-$, wherein Y is selected from the group consisting of $(aryl)_3C^+$, $(aryl)_2HC^+$, $C_7H_7^+$, $R_3NH^+$, $Ag^+$ and $(C_5R_5)_2Fe^+$, wherein R is a hydrocarbyl or substituted hydrocarbyl, A is an anion selected from the group consisting of $BF_4^-$, $PF_6^-$, $SbF_6^-$, $CF_3SO_3^-$, $CB_{11}H_{12}^-$, $CB_9H_{10}^-CB_9H_5X_5^-$, $CB_{11}H_6X_6^-$, wherein X is $F^-$, $Cl^-$, Br or $I^-$, $HBR_3^-$, wherein R is hydrocarbyl or substituted hydrocarbyl, and $[(M')Z^1Z^2 \ldots Z^n]^-$, M' is an element selected from atoms of group 13, n is the total number of Z ligands or n is 4, and $Z^1$ to $Z^n$ are independently selected from the group consisting of H radical, $C_{1-20}$ hydrocarbyl radical, substituted hydrocarbyl radical, halogens, halogen-substituted hydrocarbyl radical, hydrocarbyl-, halogen-substituted hydrocarbyl organometalloid radical, —OR, —C(O)R', —$CO_2$R', and —NR'R", wherein R' and R" are independently selected from the group consisting of H radicals, $C_{1-20}$ hydrocarbyl radical, halogens, and halogen-substituted hydrocarbyl radical; $Z^1$ to $Z^n$ radicals can be optionally linked to each other to form a stable bridging group. In the metal hydride of formula II, Cp, M and NHC are as described herein above.

The process for catalytic hydrogenation includes contacting an organic compound which contains at least one reducible functional group selected from the group consisting of $R(C{=}O)R^1$ and $R(C{=}O)H$, wherein R and $R^1$ are each independently selected from hydrogen (H) or any $C_1$–$C_{20}$ hydrocarbyl or substituted-hydrocarbyl radical with hydrogen in the presence of a catalyst to form a reaction mixture, wherein the catalyst comprises an organometallic complex described above and represented by the formula:

$$[CpM(CO)_2(NHC)L_k]^+A^- \qquad I$$

wherein Cp, M, NHC, $L_k$ and $A^-$ are as described hereinbelow.

The process for catalytic hydrosilylation includes contacting an organic compound which contains at least one functional group selected from the group consisting of $R(C{=}O)R^1$, $R(C{=}O)H$, and $R(CO_2)R^1$, wherein R and $R^1$ are each independently selected from hydrogen (H) or any $C_1$–$C_{30}$ hydrocarbyl or substituted-hydrocarbyl radical in the presence of hydrosilane with a catalyst to form a mixture, wherein the catalyst comprises an organometallic complex described above and represented by the formula:

$$[CpM(CO)_2(NHC)L_k]^+A^- \qquad I$$

wherein Cp, M, NHC, $L_k$ and $A^-$ are as described hereinbelow.

The hydrogenation process is carried out in the presence of hydrogen at a pressure from 1 atmosphere to 5000 psi, and at a temperature of from −95° C. to 120° C. Preferably, the pressure is from about 1 atmosphere to about 800 psi and the temperature is from 20° C. to 100° C. The hydrosilylation process is carried out at a temperature from about −95° C. to about 120° C. and, in one aspect of the invention, from about 20° C. to about 100° C.

The present invention also relates to an organometallic complex including a catalyst containing a transition metal, at least a ligand and a component having the formula $GAr^F$, wherein $Ar^F$ is an aromatic ring system selected from the group consisting of phenyl, naphthalenyl, anthracenyl, fluorenyl, or indenyl, said aromatic ring system having at least a substituent selected from the group consisting of fluorine, hydrogen, hydrocarbyl or fluorinated hydrocarbyl, G is substituted or unsubstituted $(CH_2)_n$ or $(CF_2)_n$, wherein n is from 1 to 30, wherein further one or more $CH_2$ or $CF_2$ groups are optionally replaced by NR, PR, $SiR_2$, BR, O or S, and R is hydrocarbyl or substituted hydrocarbyl, $GAr^F$ being covalently bonded to either said transition metal or said ligand of said catalyst, thereby rendering said cationic organometallic complex liquid.

In one aspect in the organometallic complexes of the invention the catalyst is represented by formula I $$[CpM(CO)_2(NHC)L_k]^+A^- \qquad I$$

wherein M is a metal selected from molybdenum or tungsten; Cp is substituted or unsubstituted cyclopentadienyl radical represented by the formula $C_5[Q^1Q^2Q^3Q^4Q^5]$, wherein $Q^1$ to $Q^5$ are independently selected from the group consisting of H radical, $GAr^F$, $C_{1-20}$ hydrocarbyl radical substituted hydrocarbyl radical, hydrocarbyl radical substituted by $GAr^F$, halogen radical, halogen-substituted hydrocarbyl radical, —OR, —C(O)R', —$CO_2$R', —$SiR'_3$, —NR'R" wherein R' and R" are independently selected from the group consisting of H radical, $GAr^F$, $C_{1-20}$ hydrocarbyl radical, halogen radical, and halogen-substituted hydrocarbyl radical, wherein said $Q^1$ to $Q^5$ radicals can be optionally linked to each other to form a stable bridging group; NHC is any N-heterocyclic carbene ligand, L is either any neutral ligand, wherein k is a number from 0 to 1 or L is an anionic ligand wherein k is 2, and $A^-$ is an anion.

In another aspect in the organometallic complexes of the invention, NHC is an unsubstituted or substituted N-heterocyclic carbene ligand selected from the group consisting of carbenes represented by formula III

III

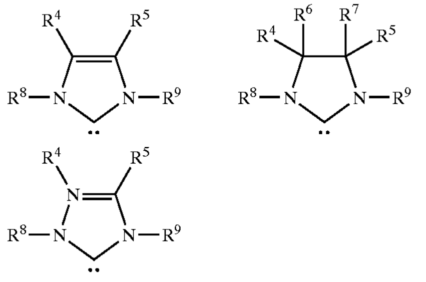

wherein $R^4$, $R^5$, $R^6$, $R^7$, $R^8$ and $R^9$ are each independently hydrogen, $GAr^F$, halogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthiol, aryl thiol, $C_1$–$C_{20}$ alkylsulfonyl and $C_1$–$C_{20}$ alkylsulfinyl, wherein further each $R^4$, $R^5$, $R^6$, $R^7$, $R^8$ and $R^9$ is optionally substituted with one or more moieties selected from the group consisting of $C_1$–$C_{20}$ hydrocarbyl, hydrocarbyl radical substituted by $GAr^F$, $C_1$–$C_{20}$ alkoxy, hydroxyl, thiol, thioether, ketone, aldehyde, ester, ether, amine, imine, amide, nitro, carboxylic acid, disulfide, carbonate, isocyanate, carbodiimide, carboalkoxy, carbamate and halogen, wherein $R^4$, $R^5$, $R^6$, $R^7$, $R^8$ and $R^9$ radicals are optionally linked to each other to form a stable bridging group.

In yet another aspect, in the organometallic complexes of the invention L is selected from the group consisting of a hydrocarbon or halogenated hydrocarbon molecule, a dihydrogen ($H_2$) or hydrosilane, a ketone, an aldehyde or an ester, an alkoxysilane, ether or alcohol molecule, a combination of two anionic ligands selected from the group consisting of hydride ($H^-$), silyl $(SiR^{10}R^{11}R^{12})^-$ and mixtures thereof, wherein $R^{10}$, $R^{11}$, $R^{12}$ are independently hydrogen, halogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthiol, aryl thiol, $C_1$–$C_{20}$ alkylsulfonyl and $C_1$–$C_{20}$ alkylsulfinyl, wherein further each $R^{10}$, $R^{11}$, $R^{12}$ is optionally substituted with one or more moieties selected from the group consisting of $C_1$–$C_{20}$ hydrocarbyl, $C_1$–$C_{20}$ alkoxy, hydroxyl, thiol, thioether, ketone, aldehyde, ester, ether, amine, imine, amide, nitro, carboxylic acid, disulfide, carbonate, isocyanate, carbodiimide, carboalkoxy, carbamate and halogen.

In another aspect in the organometallic complexes of the invention the anion ($A^-$) is selected from the group consisting of $BF_4^-$, $PF_6^-$, $SbF_6^-$, $CF_3SO_3^-$, $CB_{11}H_{12}^-$, $CB_9H_{10}^-$ $CB_9H_5X_5^-$, $CB_{11}H_6X_6^-$, wherein X is F Cl, Br or I, $HBR_3^-$, wherein R is a hydrocarbyl or substituted hydrocarbyl, and $[(M')Z^1\ Z^2 \ldots Z^n]^-$, M' is an element selected from atoms of group 13, n is the total number of Z ligands or n is 4, and $Z^1$ to $Z^n$ are independently selected from the group consisting of H radical, $GAr^F$, $C_{1-20}$ hydrocarbyl radical, substituted hydrocarbyl radical, hydrocarbyl radicals substituted by $GAr^F$, halogens, halogen-substituted hydrocarbyl radical, hydrocarbyl-, halogen-substituted hydrocarbyl organometalloid radical, —OR, —C(O)R', —$CO_2$R', and —NR'R", wherein R' and R" are independently selected from the group consisting of H radicals, $C_{1-20}$ hydrocarbyl radicals, halogens, and halogen-substituted hydrocarbyl radical; said $Z^1$ to $Z^n$ radicals optionally linked to each other to form a stable bridging group.

In another aspect the catalyst of the organometallic complex is represented by formula XI $$[CpM(CO)_2(PQ^6Q^7Q^8)L_k]^+A^- \qquad XI$$

wherein M, Cp, $Q^6$, $Q^7$, $Q^8$, $L_k$, and A are as defined herein.

In another embodiment, the invention provides a process for conducting a catalytic reaction, including contacting a reaction mixture including reactants with an organometallic complex having a catalyst containing a transition metal, at least a ligand and a component having the formula $GAr^F$, wherein $Ar^F$ is an aromatic ring system selected from the group consisting of phenyl, naphthalenyl, anthracenyl, fluorenyl, or indenyl, said aromatic ring system having at least a substituent selected from the group consisting of fluorine, hydrogen, hydrocarbyl or fluorinated hydrocarbyl, G is substituted or unsubstituted $(CH_2)_n$ or $(CF_2)_n$, wherein n is from 1 to 30, wherein further one or more $CH_2$ or $CF_2$ groups are optionally replaced by NR, PR, $SiR_2$, BR, O or S, and R is hydrocarbyl or substituted hydrocarbyl, $GAr^F$ being covalently bonded to either said transition metal or said ligand of said catalyst, thereby rendering said cationic organometallic complex liquid and recovering the catalyst after products are formed.

In yet another aspect, the catalysts of the organometallic complex of the invention include without limitation (1,5-cyclooctodiene)Ir$(PR^{C6ArF}{}_3)$(pyridine)$^+PF_6^-$, $(C_5H_5)W(CO)_2(PR^{C6ArF}{}_3)(Et_2C{=}O)^+B(C_6F_5)_4^-$, and $(C_5H_5)W(CO)_2\ (Im^{ArC6ArF})^+B(C_6F_5)_4^-$, wherein $R^{C6ArF}$ is $C_6F_5(CH_2)_6$, and $Im^{ArC6ArF}$ is represented by formula X

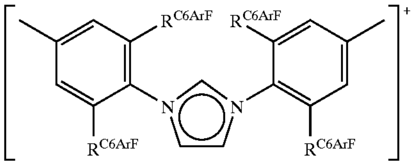
X

In yet another aspect, the invention relates to a method of preparing organometallic complexes including a catalyst containing a transition metal, a ligand and a component $GAr^F$ wherein $Ar^F$ is an aromatic ring system selected from the group consisting of phenyl, naphthalenyl, anthracenyl, fluorenyl, or indenyl, said aromatic ring system having at least a substituent selected from the group consisting of fluorine, hydrogen, hydrocarbyl or fluorinated hydrocarbyl, G is substituted or unsubstituted $(CH_2)_n$ or $(CF_2)_n$, wherein n is from 1 to 30, wherein further one or more $CH_2$ or $CF_2$ groups are optionally replaced by NR, PR, $SiR_2$, BR, O or S, and R is hydrocarbyl or substituted hydrocarbyl, $GAr^F$ being covalently bonded to either said transition metal or said ligand of said catalyst, thereby rendering said cationic organometallic complex liquid, the method including (i) providing $GAr^F$, and (ii) covalently bonding $GAr^F$ to either a metal or a ligand of said catalyst.

As a result of the present invention catalysts are provided with significantly higher lifetime and increased thermal stability. Moreover, the homogeneous organometallic Mo and W complexes of the present invention provide an effective hydrogenation or hydrosilylation catalyst at a considerably reduced cost over the prior art catalysts that use Pt, Rh, Ir or Ru complexes. As also a result of the present invention organometallic complexes including metal catalysts that exhibit behavior akin to liquid clathrates are provided that remain reactive and accessible to reagents under biphasic conditions even if the catalysts are not soluble in the reagent phase.

DETAILED DESCRIPTION OF THE INVENTION

Figure 1A:
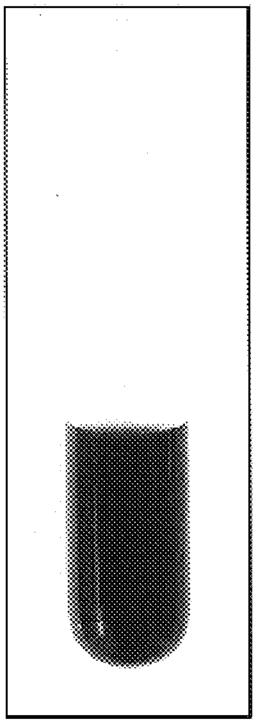
FIGS. 1A–1E are photographs illustrating the catalytic hydrosilylation of $Et_2C{=}O$ by $[CpW(CO)_2(IMes)]^+[B(C_6F_5)_4]$.
Figure 1B:
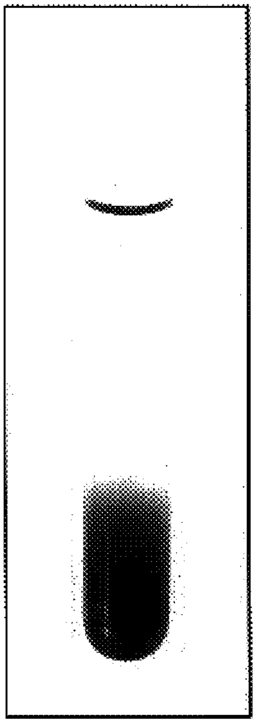

The present invention relates broadly to catalysts or catalyst precursors used for a variety of hydrogenation or hydrosilylation reactions.

Catalysts

The active catalyst of the present invention is an organometallic complex represented by the formula:

$$[CpM(CO)_2(NHC)L_k]^+A^- \qquad I$$

wherein M is a molybdenum or tungsten atom; Cp is substituted or unsubstituted cyclopentadienyl radical represented by the formula $[C_5Q^1Q^2Q^3Q^4Q^5]$, wherein $Q^1$ to $Q^5$ are independently selected from the group consisting of H radicals, hydrocarbyl radicals and substituted hydrocarbyl radicals, halogens (F, Cl, Br, I), halogen-substituted hydrocarbyl radicals, and radicals represented by —OR', —C(O)R', —$CO_2$R', —$SiR'_3$, —NR'R", wherein R' and R" are independently selected from the group consisting of H radicals, hydrocarbyl radicals, halogens, and halogen-substituted hydrocarbyl radicals), wherein $Q^1$ to $Q^5$ radicals can be linked to each other through a stable bridging group, NHC is any N-heterocyclic carbene ligand, L is either any neutral electron donor ligand, wherein k is a number from 0 to 1, or L is an anion ligand wherein k is 2, and $A^-$ is an anion. NHC can be an unsubstituted or substituted N-heterocyclic carbene selected from the group consisting of carbenes represented by formula III

III

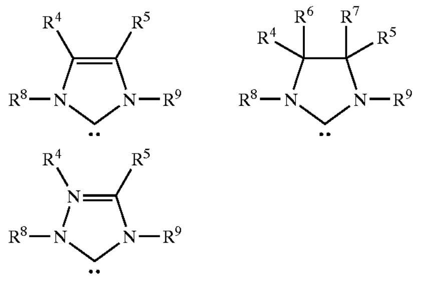

wherein $R^4$, $R^5$, $R^6$, $R^7$, $R^8$ and $R^9$ are each independently hydrogen, halogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthiol, aryl thiol, $C_1$–$C_{20}$ alkylsulfonyl and $C_1$–$C_{20}$ alkylsulfinyl. Further, each of the $R^4$, $R^5$, $R^6$, $R^7$, $R^8$ and $R^9$ radicals can be optionally substituted with one or more moieties selected from the group consisting of $C_1$–$C_{20}$ hydrocarbyl, $C_1$–$C_{20}$ alkoxy, and other functional groups, examples of which include but are not limited to hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen, wherein $R^4$, $R^5$, $R^6$, $R^7$, $R^8$ and $R^9$ radicals are optionally linked to each other to form a stable bridging group. In the metal hydride or formula II, Cp, M and NHC are as described herein above.

The inclusion of an NHC ligand in the Mo and W catalysts of the invention has been found to improve the catalytic activity of these organometallic complexes.

In another aspect of the invention, the N-heterocyclic carbene ligand is 1,3-bis(2, 4,6-trimethylphenyl)-imidazol-2-ylidene (IMes).

When NHC is IMes the catalysts of the present invention are represented by the following formula:

IV

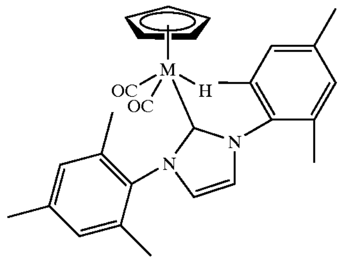

wherein M is Mo or W.

The NHC ligands described above are easily obtained in accordance with methods well known in the art such as are described by Herrmann et al. in "N-Heterocyclic Carbenes," *Angew. Chem. Int. Ed.,* 36, 2162–2187, (1997) and Herrmann et al. in "N-Heterocyclic Carbenes: A New Concept in Organometallic Catalysts," *Angew. Chem. Int. Ed.,* 41, 1290–1309, (2002) incorporated herein by reference so if set forth in full.

In an embodiment, L can be selected from the group consisting of a hydrocarbon or halogenated hydrocarbon solvent molecule, a dihydrogen ($H_2$) or dihydride $(H^-)_2$, a ketone or aldehyde substrate, a product alcohol molecule and mixtures thereof.

In another embodiment, L can be selected from the group consisting of a hydrocarbon or halogenated hydrocarbon solvent molecule, a dihydrogen ($H_2$) or hydrosilane, a ketone, an aldehyde or an ester substrate, an alkoxysilane, ether, or alcohol product molecule and mixtures thereof, or any combination of two anionic ligands such as hydride ($H^-$) and silyl $(SiR^{10}R^{11}R^{12})^-$ and mixtures thereof, wherein $R^{10}$, $R^{11}$, $R^{12}$ are independently hydrogen, halogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthiol, aryl thiol, $C_1$–$C_{20}$ alkylsulfonyl and $C_1$–$C_{20}$ alkylsulfinyl, wherein further each $R^{10}$, $R^{11}$, $R^{12}$ is optionally substituted with one or more moieties selected from the group consisting of $C_1$–$C_{20}$ hydrocarbyl, $C_1$–$C_{20}$ alkoxy, hydroxyl, thiol, thioether, ketone, aldehyde, ester, ether, amine, imine, amide, nitro, carboxylic acid, disulfide, carbonate, isocyanate, carbodiimide, carboalkoxy, carbamate and halogen.

For purposes of this invention, the term "hydrocarbon" refers to all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted having $C_{1-30}$ for nonaromatic organic compounds and $C_{3-36}$ for aromatic organic compounds.

As used herein, the term "hydrocarbyl" refers to univalent groups formed by removing a hydrogen atom from a hydrocarbon having 1–30 carbons.

As used herein, the term "substituted" includes all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxy, hydroxyalkyl, amino, aminoalkyl, halogen and the like in which the number of carbons can range from 1 to about 30. The permissible substituents can be one or more and the same or different for appropriate organic compounds. This invention is not intended to be limited in any manner by the permissible substituents of organic compounds.

As used herein, the term "aryl" refers to an aromatic cyclic structure containing at least one monocyclic carbon ring including without limitation phenyl, naphthyl, anthracenyl and the like. "Substituted aryl" refers to an aryl group substituted with substituents as defined hereinabove.

As used herein "biphasic solution" refers to a solution that has two distinct phases.

Anion ($A^-$) can be selected from the group consisting of $HBR_3^-$, wherein R is a hydrocarbyl or substituted hydrocarbyl, $BF_4^-$, $PF_6^-$, $SbF_6^-$, $CF_3SO_3^-$, $CB_{11}H_{12}^-$, $CB_9H_{10}^-$, $CB_9H_5X_5^-$, $CB_{11}H_6H_6^-$, wherein X is F, Cl, Br and I, and $[(M')Z^1\ Z^2\ \ldots\ Z^n]^-$ wherein, M' is an element selected from the atoms of group 13; n is the total number of Z ligands, and $Z^1$ to $Z^n$ are independently selected from the group consisting of H radicals, $C_1$–$C_{20}$ hydrocarbyl radicals and substituted hydrocarbyl radicals, halogens (F, Cl, Br, I), halogen-substituted hydrocarbyl radicals, hydrocarbyl- and halogen-substituted hydrocarbyl organometalloid radicals, and radicals represented by the formulas —OR', —C(O)R', —$CO_2$R', —NR'R", wherein R' and R" are independently selected from the group consisting of H radicals, $C_1$–$C_{20}$ hydrocarbyl radicals, halogens, and halogen-substituted hydrocarbyl radicals; $Z^1$ to $Z^n$ radicals can be optionally linked to each other to form a stable bridging group. In another aspect, the total number of Z ligands is four.

M' can be any metal of group 13 of the Periodic Table of Elements as published by CRC Press, Inc., 1984 including but not limited to boron, aluminum or gallium. $Z^1$ to $Z^n$ are each fluorine substituted phenyl, naphtyl or anthracenyl radicals.

In another embodiment, the catalysts of the present invention can further include a solvent of crystallization thereby forming $[CpW(CO)_2\ (NHC)L_k]^+[A]^-\cdot Y'_h$, wherein h is a number from 0 to 2 and Y' is selected from the group consisting of any hydrocarbon, aromatic hydrocarbon, halocarbon, or ether, examples of which include but are not limited to hexane, benzene, toluene, tetrahydrofuran, diethyl ether and mixtures thereof.

The catalysts of the present invention have novel and valuable properties. For example, a stability at room temperature (about 23° C.) and a useful combination of solubility properties allows the use of the catalyst in "neat" or pure reagents, i.e., in the absence of a solvent. Another characteristic is that whenever the substrates do not have aromatic groups, the catalysts precipitate upon completion of the hydrosilylation reaction, and can be efficiently recovered from the reaction mixtures and reused. Thus many catalysts of the present invention are recyclable.

In one aspect, the catalysts of the present invention are "clathrate-enabled." As used herein "clathrate-enabled" refers to catalysts that exhibit the behavior of inclusion compounds or liquid clathrates. In their clathrate-enabled form, the organometallic complexes of the present invention are liquid and can retain their catalytic activity in a solvent free reaction until all of the liquid substrates are converted to liquid products. At the end of the catalytic reaction, the liquid catalysts, in some cases, revert to their solid state and can be recovered as precipitates by simply decanting the products of the reaction.

In catalytic reactions, the cationic clathrate-enabled catalysts of the invention are found in the presence of weakly coordinating counterions, anions, $A^{31}$ as defined hereinabove. In one aspect, the anions include a fluorinated organic fragment, such as for example $C_6F_5$. These types of organometallic complexes do not readily form crystalline lattices but remain as liquids, exhibiting behavior like that of metastable inclusion compounds and liquid clathrates.

Method of Making the Catalysts

The catalysts of the present invention are prepared by reacting a metal hydride represented by the formula CpM$(CO)_2$(NHC)H with a hydride removing agent selected from $BR_3$ or a compound represented by formula $Y^+A^-$, wherein $Y^+$ is selected from the group consisting of $(aryl)_3C^+$, $(aryl)_2HC^+$, $C_7H_7^+$, $R_3NH^+$, $Ag^+$ and $(C_5R_5)_2Fe^+$, wherein R is a hydrocarbyl radical or substituted hydrocarbyl radical, $A^-$ is an anion selected from the group consisting of $BF_4^-$, $PF_6^-$, $SbF_6^-$, $CF_3SO_3^-$, $CB_{11}H_{12}^-$, $CB_9H_{10}^-CB_9H_5X_5^-$, $CB_{11}H_6X_6^-$, wherein X is F, Cl, Br or I, $HBR_3^-$, wherein R is a hydrocarbyl radical or subsubstituted hydrocarbyl radical, and $[(M')Z^1Z^2 \ldots Z^n]^-$, M' is an element selected from atoms of group 13, n is the total number of Z ligands or n is 4, and $Z^1$ to $Z^n$ are independently selected from the group consisting of H radical, $C_{1-20}$ hydrocarbyl radical, substituted hydrocarbyl radical, halogens, halogen-substituted hydrocarbyl radical, hydrocarbyl-, halogen-substituted hydrocarbyl organometalloid radical, —OR, —C(O)R', —$CO_2$R', and —NR'R", wherein R' and R" are independently selected from the group consisting of H radicals, $C_{1-20}$ hydrocarbyl radical, halogens, and halogen-substituted hydrocarbyl radical; said $Z^1$ to $Z^n$ radicals optionally linked to each other to form a stable bridging group.

In one aspect, the hydride removing agent is $Ph_3C^+A^-$, wherein Ph is $C_6H_5$ and $A^-$ is an anion as described hereinabove.

The metal hydride represented by the formula CpM$(CO)_2$(NHC)H is prepared by reacting a metal phosphine hydride represented by the formula CpM$(CO)_2(PR_3)$H, wherein R is any $C_1$–$C_{20}$ alkyl or $C_6$–$C_{36}$ aryl group and combination thereof with NHC, which is as described herein above.

The active catalyst can be prepared prior to being mixed with the organic compound that is being hydrogenated or hydrosilylated, or it can be generated in the reaction mixture. When the catalyst is prepared in the reaction mixture, the metal hydride can be mixed with the hydride removing agent.

Clathrates are generally formed only when either reagents or products have a suitable structure to form inclusion compounds with the catalyst. Suitable structures include without limitation small aromatic molecules. In one aspect of the clathrate-enabled catalysts of the present invention the clathrate-like phase can be forced to form even in the absence of suitable reagents or products. It is important that the "clathrate-enabled" catalysts include an aromatic ring usually fluorinated, linked to the catalyst by a long, flexible tether or bridge that can be several carbons long. For example a suitable structure that can be used to form liquid clathrates is represented by formula V:

V

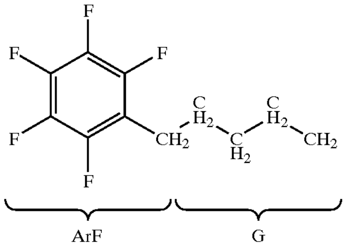

In formula V, $Ar^F$ is an aromatic ring system selected from the group consisting of phenyl, naphthalenyl, anthracenyl, fluroenyl and indenyl, the aromatic ring having a substituent selected from the group consisting of fluorine, hydrogen, hydrocarbyl, fluorinated hydrocarbyl. The tether or bridge G is a flexible hydrocarbon $(CH_2)_n$ or $(CF_2)_n$, wherein n is 1 to 30, and G can be fully or partially fluorinated. G can optionally contain heteroatoms such as N, P, Si, O, B or S, wherein one or more $CH_2$ groups can be replaced by a moiety selected from the group consisting of NR, PR, $SiR_2$, BR, O, and S, wherein R is hydrocarbyl or substituted hydrocarbyl group.

Cationic organometallic complexes containing one or more $GAr^F$ moieties, are prepared from halide derivatives of $GAr^F$ such as $ClGAr^F$, $BrGAr^F$, or $IGAr^F$. Synthetic procedures useful to prepare halide derivatives of $GAr^F$ are known in the art. For example, $C_6F_5CF_2CF_2$ Br can be prepared according to a procedure described in Yang, et al., 2000. Other $IGAr^F$ compounds can be prepared according to the procedure set forth in equation (1) below:

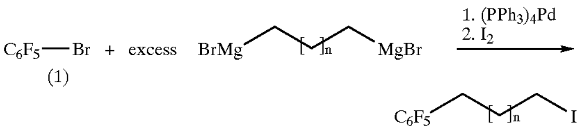

The fluorination of the aromatic ring imparts to the catalyst the desired solubility characteristics, i.e., the catalyst can be immiscible with the solvents and reagents at the end of the catalytic reaction. In addition, the catalysts can in some cases have little miscibility even during the reaction. The presence of multiple fluorine atoms provides the desirable property of making the catalysts more soluble at higher temperatures than at lower temperatures, thus facilitating improved separation and recovery of the catalyst at room temperature at the completion of the reaction. Suitable fluorinated aromatic ring include without limitation $C_6F_5$ and also condensed or fused rings such as a fluorinated naphthalene or anthracene. An example of GArF including a fluorinated naphthalene is shown in Formula VI below:

VI

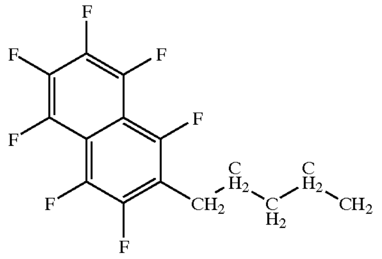

In another aspect, at least one fluorine on the aromatic ring, can be replaced with other substituents, such as for example, a hydrogen, hydrocarbyl or fluorinated hydrocarbyl group. The flexible hydrocarbon bridge can be used to connect the fluorinated aromatic ring to the molecule of the catalyst.

In an embodiment, any transition metal catalyst capable of forming a covalent bond with a moiety such as $GAr^F$ can form a liquid clathrate and can be used as a recyclable catalyst including cases of solvent-free catalysis. Catalysts that can form a covalent bond with $GAr^F$ include without limitations homogeneous catalysts of the formula I $$[CpM(CO)_2(NHC)L_k]^+A^-$$

as defined hereinabove. $GAr^F$ can covalently bond to the ligand L or to the meal M. In catalysts other than those of formula I, $GAr^F$ can form a covalent bond with any transition metal. Transition metals are elements in groups 3 to 12 of the Table of Elements. $GAr^F$ can also covalently bond to ligands of the catalyst such as for example a cyclopentadienyl, phosphine or N-heterocyclic carbene ligand. Examples of catalysts of the formula I bonded to $GAr^F$ are shown in formulas VII, VIII and IX below:

VII

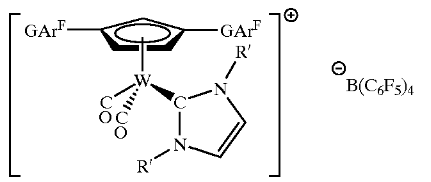

R′ = any alkyl or aryl group

VIII

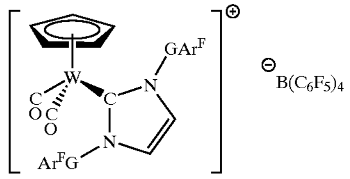

IX

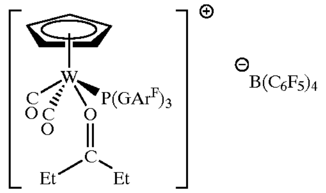

Formulas VII and VIII illustrate the catalyst of formula I as a cationic unsaturated complex. Formula IX shows the catalyst as a phosphine ketone complex.

Other solid catalysts can become liquids and maintain their liquid form until all reactants in the solvent-free reaction are converted into products. Useful catalysts include without limitation (1,5-cyclooctodiene) $Ir(PR^{C6ArF}_3)(pyridine)^+PF_6^-$; $(C_5H_5)W(CO)_2(PR^{C6ArF}_3)(Et_2C{=}O)^+B(C_6F_5)_4^-$; and $(C_5H_5)W(CO)_2(Im^{ArC6ArF})^+B(C_6F_5)_4^-$, wherein $R^{C6ArF}$ is $C_6F_5(CH_2)_6$, and $Im^{ArC6ArF}$ is represented by formula X

X

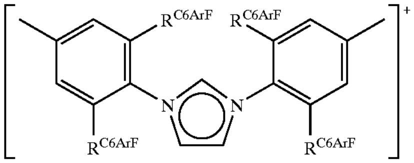

(1,5-cyclooctodiene)$Ir(PR^{C6ArF}_3)(pyridine)^+PF_6^-$ is a catalyst useful for hydrogenation of alkenes, including tetra-substituted alkenes.

In another aspect of the invention, the catalytic organometallic complex is formed by covalently bonding $GAr^F$ to a phosphine ligand of a catalyst of formula XI $$[CpM(CO)_2(PQ^6Q^7Q^8)L_k]^+A^- \quad \text{XI}$$

wherein M is a molybdenum or tungsten atom; Cp is substituted or unsubstituted cyclopentadienyl radical represented by the formula $[C_5Q^1Q^2Q^3Q^4Q^5]$, wherein $Q^1$ to $Q^5$ are independently selected from the group consisting of H radical, $GAr^F$, $C_{1-20}$ hydrocarbyl radical substituted hydrocarbyl radical, including hydrocarbyl radicals substituted by $GAr^F$, halogen radical, halogen substituted hydrocarbyl radical, —OR, —C(O)R', —$CO_2$R', —$SiR'_3$, —NR'R" wherein R' and R" are independently selected from the group consisting of H radical, $C_{1-20}$ hydrocarbyl radical, halogen radical, and halogen-substituted hydrocarbyl radical, wherein said $Q^1$ to $Q^5$ radicals can be optionally linked to each other to form a stable bridging group; $PQ^6Q^7Q^8$ is a phosphine ligand, wherein $Q^6$, $Q^7$, $Q^8$ represent three groups independently selected from the group consisting of H radical, $GAr^F$, $C_{1-20}$ hydrocarbyl radical substituted hydrocarbyl radical, including hydrocarbyl radicals substituted by $GAr^F$, halogen radical, halogen substituted hydrocarbyl radical, —OR, —C(O)R', —$CO_2$R', —$SiR'_3$, —NR'R" wherein R' and R" are independently selected from the group consisting of H radical, $C_{1-20}$ hydrocarbyl radical, halogen radical, and halogen-substituted hydrocarbyl radical, wherein all three $Q^6$, $Q^7$, $Q^8$ groups can be the same or different or two of the three groups can be the same; L is either any neutral ligand, wherein k is a number from 0 to 1 or L is an anionic ligand wherein k is 2, and $A^-$ is an anion. In the catalyst of formula XI, L is selected from the group consisting of a hydrocarbon or halogenated hydrocarbon molecule, a dihydrogen ($H_2$) or hydrosilane, a ketone, an aldehyde or an ester, an alkoxysilane, ether or alcohol molecule, a combination of two anionic ligands selected from the group consisting of hydride ($H^-$), silyl $(SiR^{10}R^{11}R^{12})^-$ and mixtures thereof, wherein $R^{10}$, $R^{11}$, $R^{12}$ are independently hydrogen, halogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthiol, aryl thiol, $C_1$–$C_{20}$ alkylsulfonyl and $C_1$–$C_{20}$ alkylsulfinyl, wherein further each $R^{10}$, $R^{11}$, $R^{12}$ is optionally substituted with one or more moieties selected from the group consisting of $C_1$–$C_{20}$ hydrocarbyl, $C_1$–$C_{20}$ alkoxy, hydroxyl, thiol, thioether, ketone, aldehyde, ester, ether, amine, imine, amide, nitro, carboxylic acid, disulfide, carbonate, isocyanate, carbodiimide, carboalkoxy, carbamate and halogen; wherein the anion $A^-$ is as described above, namely selected from the group consisting of $BF_4^-$, $PF_6^-$, $SbF_6^-$, $CF_3SO_3^-$, $CB_{11}H_{12}^-$, $CB_9H_{10}^-CB_9H_5X_5^-$, $CB_{11}H_6X_6^-$, wherein X is F Cl, Br or I, $HBR_3^-$, wherein R is a hydrocarbyl or substituted hydrocarbyl, and $[(M')Z^1Z^2 \ldots Z^n]^-$, M' is an element selected from atoms of group 13, n is the total number of Z ligands or n is 4, and $Z^1$ to $Z^n$ are independently selected from the group consisting of H radical, $GAr^F$, $C_{1-20}$ hydrocarbyl radical, substituted hydrocarbyl radical, hydrocarbyl radicals substituted by $GAr^F$, halogens, halogen-substituted hydrocarbyl radical, hydrocarbyl-, halogen-substituted hydrocarbyl organometalloid radical, —OR, —C(O)R', —$CO_2$R', and —NR'R", wherein R' and R" are independently selected from the group consisting of H radicals, $C_{1-20}$ hydrocarbyl radicals, halogens, and halogen-substituted hydrocarbyl radical; said $Z^1$ to $Z^n$ radicals optionally linked to each other to form a stable bridging group. Catalysts of formula XI are prepared as described in U.S. Pat. No. 6,124,509 to Voges, M. H. and Bullock, R. M., incorporated herein by reference as if set forth in full.

The resulting catalytic organometallic complex having a phosphine ligand includes, for example, a catalyst of the formula XII $$(C_5H_5)W(CO)_2(PR^{C6ArF}{}_3)(Et_2C{=}O)^+B(C_6F_5)_4^- \qquad \text{XII}$$

Method of Using the Organometallic Complexes

The organometallic complexes of the present invention can be used broadly as catalysts for hydrogenation or hydrosilylation reactions.

The present invention provides a process for hydrogenating of ketones and aldehydes to alcohols using organometallic molybdenum and tungsten complexes as catalysts.

Using the process of this invention, unsaturated organic compounds can be hydrogenated to give the corresponding saturated derivatives. Organic compounds which may be hydrogenated in accordance with the present invention include but are not limited to ketones and aldehydes.

In an aspect, the organic compound that is hydrogenated can be represented by at least one reducible functional group selected from the group consisting of $R^1(C{=}O)R^2$ and $R^1(C{=}O)H$, wherein $R^1$ and $R^2$ are each independently selected from any $C_1$–$C_{20}$ hydrocarbyl group. The hydrogenation of ketones and aldehydes involves the overall addition of two hydrogen atoms to the carbon-oxygen double bond to result in the formation of the corresponding alcohol.

The hydrogenation process of the invention includes contacting aldehydes or ketones with hydrogen in the presence of the organometallic catalyst of the invention that is represented by the formula I:

$$[CpM(CO)_2(NHC)L_k]^+A^- \qquad \text{I}$$

wherein M is a molybdenum or tungsten atom, Cp is substituted or unsubstituted cyclopentadienyl radical represented by the formula $[C_5Q^1Q^2Q^3Q^4Q^5]$, wherein $Q^1$ to $Q^5$ are independently selected from the group consisting of H radicals, $C_1$–$C_{20}$ hydrocarbyl radicals and substituted hydrocarbyl radicals, halogens (F, Cl, Br, I), halogen-substituted hydrocarbyl radicals, and radicals represented by the formulas —OR', —C(O)R', —$CO_2$R', —$SiR'_3$, —NR'R", wherein R' and R" are independently selected from the group consisting of H radicals, hydrocarbyl radicals, halogens, and halogen-substituted hydrocarbyl radicals, said $Q^1$ to $Q^5$ radicals can optionally be linked to each other to form a stable bridging group; NHC is any N-heterocyclic carbene ligand, L is either any neutral electron donor ligand, k is a number from 0 to 1 or L is an anionic ligand, wherein k is 2, and $(A^-)$ is an anion as described hereinabove.

NHC can be an unsubstituted or substituted N-heterocyclic carbene as was more specifically described hereinabove. In an embodiment NHC can be IMes.

In a hydrogenation process, L can be selected from the group consisting of a hydrocarbon or halogenated hydrocarbon solvent molecule, a dihydrogen ($H_2$) or dihydride $(H^-)_2$, a ketone or aldehyde substrate, a product alcohol molecule and mixtures thereof.

Anion $(A^-)$ can be selected from the group consisting of $BF_4^-$, $PF_6^-$, $SbF_6^-$, $CF_3SO_3^-$, $CB_{11}H_{12}^-$, $CB_9H_{10}^-$, $CB_9H_5X_5^-$, $CB_{11}H_6X_6^-$, wherein X is F, Cl, Br or I, $HBR_3^-$, wherein R is a hydrocarbyl radical or substituted hydrocarbyl radical, and $[(M')Z^1Z^2 \ldots Z^n]^-$ as was more specifically described hereinabove.

The present invention also provides a process for hydrosilylation of ketones, aldehydes and esters to alkoxysilanes, ethers or alcohols using organometallic molybdenum and tungsten complexes of the invention as the catalysts. The organic compound that can be hydrosilylated contains at least one reducible functional group selected from the group consisting of $R(C{=}O)R^1$, $R(C{=}O)H$ or $R^1(CO_2)R^2$, wherein $R^1$ and $R^2$ are each independently selected from hydrocarbyl radicals or substituted-hydrocarbyl radicals, which can be the same or different.

The hydrosilylation process includes contacting aldehydes, ketones or esters with hydrosilanes in the presence of the organometallic catalyst of the present invention as described herein above.

In a hydrosilylation process, L can be selected from the group consisting of a hydrocarbon or halogenated hydrocarbon solvent, a dihydrogen ($H_2$) or hydrosilane, a ketone, an aldehyde or an ester substrate, an alkoxysilane, ether, or alcohol product molecule and mixtures thereof, or any combination of two anionic ligands such as hydride ($H^-$) and silyl $(SiR^{10}R^{11}R^{12})^-$, wherein $R^{10}$, $R^{11}$ and $R^{12}$ are each independently hydrogen, halogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthiol, aryl thiol, $C_1$–$C_{20}$ alkylsulfonyl and $C_1$–$C_{20}$ alkylsulfinyl, wherein further each $R^{10}$, $R^{11}$, $R^{12}$ is optionally substituted with one or more moieties selected from the group consisting of $C_1$–$C_{20}$ hydrocarbyl, $C_1$–$C_{20}$ alkoxy, hydroxyl, thiol, thioether, ketone, aldehyde, ester, ether, amine, imine, amide, nitro, carboxylic acid, disulfide, carbonate, isocyanate, carbodiimide, carboalkoxy, carbamate and halogen.

Hydrosilylation of ketone is of synthetic interest because when followed by hydrolysis of the resulting alkoxysilane, this reaction provides a mild route for reducing ketones to secondary alcohols.

The hydrogenation and hydrosilylation processes of the present invention can be carried out over a wide range of temperatures and pressures. For example, the pressure of hydrogen in the hydrogenation reactions can vary over a range from about 1 atmosphere to about 5,000 psi, the temperature can vary over a range from −95° C. to about 120° C. Nevertheless, the processes of the present invention can be conducted under mild conditions of temperatures and pressures including without limitations 1 atmosphere and room temperature of about 23° C. In certain embodiments the pressure can range from about 1 atmosphere to about 800 psi and the temperature from about 20° C. to about 100° C. The temperature range for hydrosilylation reactions is from about −95° C. to about 120° C. and, in another aspect of the invention, from about 20° C. to about 100° C.

Various solvents may be used with the inventive methods of hydrogenation or hydrosilylation.

Any solvent which is chemically inert, which does not interfere with the hydrogenation or hydrosilylation reaction and which at least partially dissolves the catalyst may be employed. The solvents can be aromatics such as toluene, xylene, mesitylene and benzene or halogenated aromatics and other well known solvents such as hexane, tetrahydrofuran and diethyl ether. If the reactants are mutually soluble, the use of a solvent is not necessary and the catalysts can catalyze the reaction in the absence of a solvent as "neat" reagents. In addition, the substrate, either a ketone, aldehyde or ester, can be partially soluble or it can be completely soluble in the solvent.

The active catalyst can be prepared prior to being mixed with the organic compound that is being hydrogenated or hydrosilylated and it can also be generated in the reaction mixture. When the catalyst is prepared in the reaction mixture, the metal hydride is mixed with hydride removing agent as described hereinabove.

The processes of the invention can be conducted in any type of apparatus that enables intimate contact of the reactants and control of operating conditions. The hydrogenated product may be removed by known means such as distillation and/or chromatography.

To explore the process of self-separation for solvent free reactions, two cationic complexes with weakly coordinating $B(C_6F_5)_4^-$ anions have been used as catalysts for hydrosilylation of carbonyl compounds: $[CpM(CO)_2(IMes)]^+[B(C_6F_5)_4]^-$ wherein Cp is cyclopentadienyl, IMes is 1,3-bis (2,4,6-trimethylphenyl)-imidazol-2-ylidene, and M is Mo or W, also identified as complex 1Mo and 1W, respectively. Hydrosilylation is a suitable model reaction as it starts with a polar liquid substrate, such as ketone or ester, and ends with a non-polar liquid product like alkoxysilane as shown in equation (1) below.

(2)

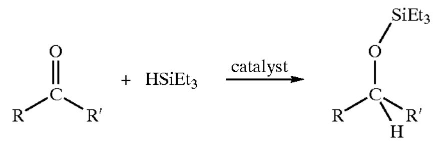

Hydrosilylation is also a reaction of considerable practical interest as it is widely used for both large and small scale syntheses. Not only are alkoxysilanes precursors to silicon-containing polymers and ceramic materials, but they are also valuable in organic synthesis. Thus, for the conversion of carbonyl compounds to alcohols, hydrosilylation is often utilized as a convenient alternative to hydrogenation, particularly in asymmetric synthesis.

We have previously found 1Mo and 1W to be soluble in ketones, insoluble in non-polar hydrocarbon solvents, and likely to the form oily precipitates such as liquid clathrates instead of crystalline products. We have also found that the N-heterocyclic carbene ligand, IMes, stabilizes the electronically unsaturated $16e^-$ 1Mo and 1W complexes by formation of a weak bond between the metal center and one of the C═C double bonds of a mesityl group as described in Dioumaev, V. K., et al., 2003.

Complexes 1W and 1Mo could catalyze hydrosilylation of carbonyl compounds under mild conditions. The reactions exhibited good rates, high conversions, and an excellent selectivity for hydrosilylation of C═O as opposed to C═C double bonds as shown in Table 1 below.

TABLE 1

Hydrosilylation of carbonyl compounds by W catalysts

| substrate | products | initial TOF $h^{-1}$ | total TON | yield % | time h |
|---|---|---|---|---|---|
| 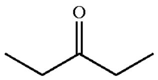 | 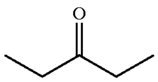 | 370 | 446 | 89 | 1 |

TABLE 1-continued

| Hydrosilylation of carbonyl compounds by W catalysts | | | | | |
|---|---|---|---|---|---|
| substrate | products | initial TOF $h^{-1}$ | total TON | yield % | time h |
| | 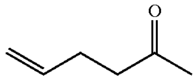 | 20 | 36 | 7 | |
| | 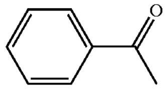 | ~5 | 15 | 3 | |
| 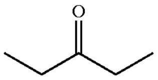 | 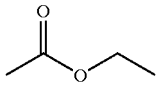 | >2000 | 447 | 93 | 0.25[a] |
| | 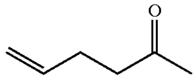 | >100 | 24 | 5 | |
| 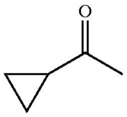 | 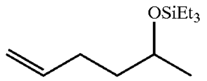 | 150 | 489 | 98 | 19 |
| 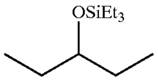 | 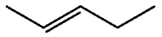 | 110 | 446 | 89 | 23 |
| | 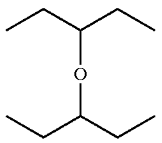 | <5 | 11 | 2 | |
| 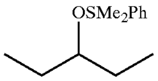 | $EtOSiEt_3$ | 170 | 468 | 94 | 26[b] |
| | $Et_2O$ | <1 | 30 | 6 | |
| 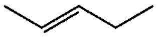 | 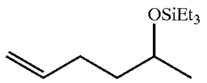 | 30 | 386 | 77 | 168 |
| | 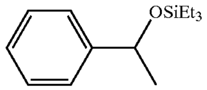 | <1 | 70 | 14 | |

Reactions were conducted at 23° C. in neat liquid substrates without solvent: ketone/$HSiEt_3$/1W=100/120/0.2. Turnover number (TON) is the number of moles of a carbonyl substrate consumed to yield a given product per the number of moles of catalyst. TOF is the average initial turnover frequency measured within the first 15–20 minutes of the reaction (TOF=TON/time). [a]$HSiMe_2Ph$ was used instead of $HSiEt_3$. [b]The ratios were: ester/$HSiEt_3$/1W=100/220/0.2; Total TON is a total number of turnovers for a given product, measured at the end of the reaction.

Figure 1C:
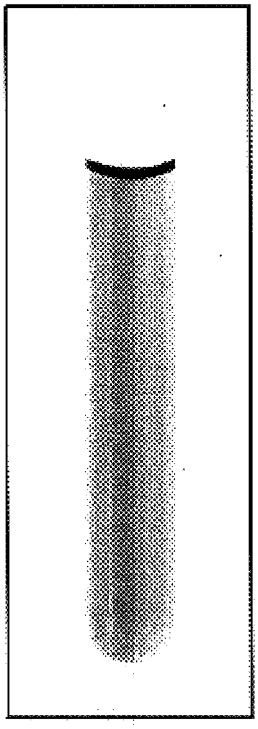
Figure 1D:
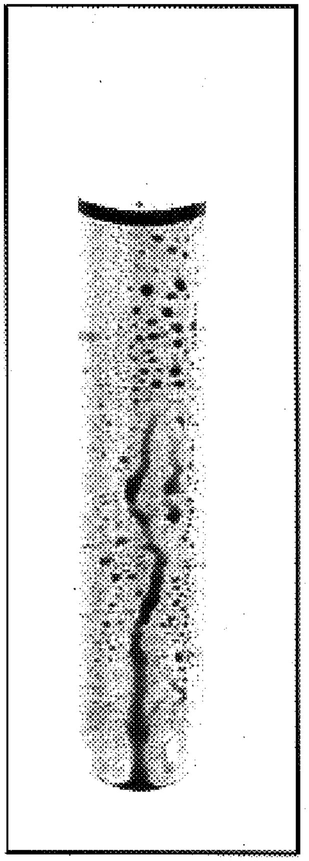
Figure 1E:
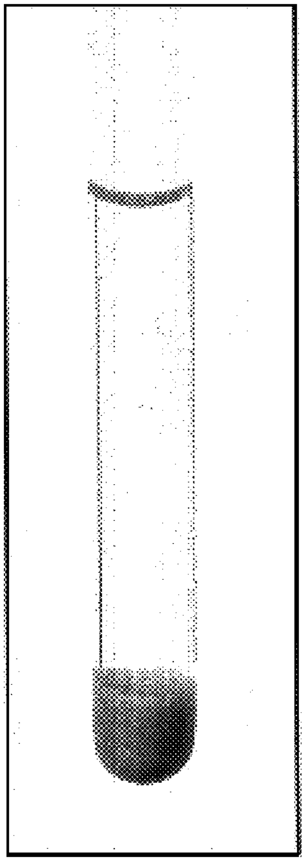

Hydrosilylation of aromatic substrates yields a brown oily precipitate toward the end of reaction, but some of the catalyst remains soluble. Similarly, hydrosilylation with an aromatic silane, such as $(CH_3)_2PhSiH$, also results in a partially soluble catalyst and a small amount of a brown oily precipitate. Aliphatic substrates, on the other hand, yield colorless solutions at the end of the reaction with no detectable soluble metal-containing species in the proton nuclear magnetic resonance ($^1H$ NMR) spectra. Conversion of the last traces of the carbonyl substrate can be monitored visually as the precipitate transforms from a purple oil into a pale yellow solid as illustrated in FIGS. 1A to E. In FIG. 1A the ketone complex 4W is shown before adding $HSiEt_3$ FIG. 1B is a photograph showing the reaction mixture when $HSiEt_3$ added but it has not yet mixed. FIG. 1C shows the reaction mixture after $HSiEt_3$ is mixed and the reaction mixture is homogeneous. FIG. 1D shows the reaction mixture when a liquid clathrate is formed. The catalytic reaction is nearing completion. FIG. 1E shows the end of reaction when the catalyst has precipitated.

Fortunately, the precipitate is somewhat sticky and can be readily recovered by decanting the liquid products without any special precautions to retain the catalyst, and no solvent is needed for the reaction work-up.

The actual resting state of the tungsten catalyst that is recycled has been found to be a mixture of $[CpW(CO)_2(IMes)(SiEt_3)H]^+[B(C_6F_5)_4]^-$ (2W) and $[CpW(CO)_2(IMes)(H)_2]^+[B(C_6F_5)_4]^-$ (3W). The assignment was confirmed by the independent syntheses of both compounds from 1W and $HSiEt_3$ or dihydrogen. The solubility of 2W and 3W in the products of hydrosilylation of $Et_2C{=}O$ was below the detection limits of $^1H$ NMR spectroscopy. The residual solubility of all species with a $B(C_6F_5)_4^-$ counterion was measured by fluorine nuclear magnetic resonance ($^{19}F$ NMR) spectroscopy to be about $4\times10^{-4}$ mol $L^{-1}$, which corresponded to about 5% of the loaded 0.2 mol % catalyst. In other words, more than 95% of the loaded catalysts precipitated as the resting state, and was available for recycling. The recovered catalyst exhibited up to twice the activity after the first recycle, and retained good activity for all five cycles performed as illustrated in Table 2 below, wherein the reaction conditions and TOF are the same as in Table 1 above.

TABLE 2

Recycling of catalyst for the hydrosilylation of $Et_2C{=}O$.

| Cycle No. | 1 | 2 | 3 | 4 | 5 |
|---|---|---|---|---|---|
| time of measurement, min | 15 | 10 | 10 | 10 | 10 |
| TOF ($h^{-1}$) | 370 | 780 | 870 | 760 | 620 |

Thus, both 2W and 3W, were good catalyst precursors.

The ketone complex $[CpW(CO)_2(IMes)(Et_2C{=}O)]^+[B(C_6F_5)_4]^-$ (4W) was also a resting state present during hydrosilylation of $Et_2C{=}O$, giving a purple color to the reaction mixture ($\lambda_{max}$(toluene)=498 nm, $\epsilon=1\times10^3$ L $mol^{-1}$ $cm^{-1}$). Identified by multinuclear NMR and infrared (IR) spectroscopy, the assignment of 4W was confirmed by an independent synthesis from 1W and $Et_2C{=}O$. Complex 4W was most abundant at the beginning of the hydrosilylation and is gradually replaced by 2W and 3W. The formation of the dihydride complex 3W was due to traces of $H_2$ produced from $HSiEt_3$ and residual water. The equilibrium for the formation of 3W is very favorable. $K_{eq}=[3W][Et_2C{=}O]/[4W][H_2]\approx1\times10^3$ at 298° K. as determined by $^1H$ NMR. $[H_2]$ was corrected for the presence of 25% of para-$H_2$, which is NMR-silent. As is often the case with excessively stable compounds, 3W could inhibit hydrosilylation. The origin of inhibition was readily traced to the presence of dihydrogen. Thus, reaction in a vial open to an inert atmosphere showed an almost three-fold acceleration in initial turnover frequency compared to the same reaction in a closed tube. We note that both samples were maintained homogeneous to eliminate uncertainties of precipitation and were taken from the very same stock solution of acetophenone, $HSiEt_3$, and 1W.

In an aspect of the present invention, the catalyst activity and solubility at the final stages of the reaction of aliphatic substrates was determined by the formation of the liquid clathrate, which was metastable. This clathrate could change its composition rapidly into a solid. The liquid clathrates formed with aromatic substrates tended to be more stable and was analyzed more easily. Thus a liquid clathrate formed in the course of hydrosilylation of acetophenone was characterized by $^1H$ NMR to have a composition of about 3.4 equivalents of the alkoxysilane $Ph(Me)CH{-}OSiEt_3$ per equivalent of tungsten. Note that this particular liquid clathrate was not critical to the catalyst activity, as the catalyst was somewhat soluble in the aromatic substrates anyway. In a broader sense, however, the characterization of this clathrate illustrates how only a few equivalents of the right component can retain the catalyst in a liquid phase, even if it is not soluble in the bulk of the reaction mixture.

EXAMPLES

The following non-limiting examples are illustrative of the present invention. It should be noted that various changes could be made in the examples and processes therein without departing from the scope of the present invention. For this reason, it is intended that the embodiments of the present application should be interpreted as being illustrative and not limiting in any sense.

Instrumentation

All operations were performed in Schlenk-type glassware on a dual-manifold Schlenk line or in a argon-filled Vacuum Atmospheres glove box. NMR spectra were obtained on Bruker Avance-400 FT NMR spectrometer (400 MHz for $^1H$). All NMR spectra were recorded at 25° C. unless stated otherwise. Chemical shifts for $^1H$ and $^{13}C$ NMR spectra were referenced using internal solvent resonances and are reported relative to tetramethylsilane. External standards of trifluorotoluene (set as $\delta=-63.73$) and 85% $H_3PO_4$ (set as $\delta=0$) were used for referencing $^{19}F$ and $^{31}P$ NMR spectra. $^{13}C\{^1H\}$ and $^{31}P\{^1H\}$ NMR spectra were recorded with broadband $^1H$ decoupling unless stated otherwise. For quantitative $^1H$ NMR measurements the relaxation delay was set at 30 seconds. GC-MS spectra were recorded on an Agilent Technologies 5973 mass selective detector connected to an Agilent Technologies 6890N gas chromatograph equipped with an HP-5 ms column (5% phenyldimethylpolysiloxane). Infrared spectra were recorded on a Mattson Polaris spectrometer. Elemental analyses were performed by Schwarzkopf Microanalytical Laboratory, Inc. (Woodside, N.Y.). Unless specified otherwise, the materials used in these examples are readily commercially available.

Turnover Measurement

In the experiments described below turnovers are the numbers of moles of a carbonyl compound hydrogenated or hydrosilylated per mole of catalyst.

For example, in the hydrogenation of 3-pentanone the total turnover number [TON(total)] includes the alcohol (3-pentanol) formed by hydrogenation of the ketone, plus the ether $(Et_2CH)_2O$ formed through condensation of two molar equivalents of the alcohol. Each equivalent of ether is counted as representing two hydrogenation equivalents (or turnovers of the catalyst), since it takes two alcohols to form one ether.

For hydrosilylation reactions turnover numbers for every product are reported separately. Each equivalent of an ether (R(R')HCOCH(R')R) formed in a hydrosilylation of a ketone (R(R')C=O) is counted as representing two turnovers of the catalyst, since it takes two ketones to form one ether. However, each equivalent of an ether ($RCH_2OR'$) formed in a hydrosilylation of an ester ($RCO_2R'$) is counted as representing one turnover of the catalyst, since it takes one ester to form one ether. Each equivalent of an alkoxysilane ($RCH_2OSiEt_3$ or $R'OSiEt_3$) formed in a hydrosilylation of an ester ($RCO_2R'$) is counted as representing 0.5 turnover of the catalyst, since it takes one ester to form two alkoxysilanes.

Examples 1 to 9 describe the syntheses of catalysts and catalyst precursors. Many of the materials used in Examples 1 to 9 are readily commercially available. Others such as $CpMo(CO)_2(PPh_3)H$ and $CpW(CO)_2(PPh_3)H$ are easily prepared by procedures available in scientific publications such as described by Bainbridge, A., et al., *J. Chem. Soc.* (*A*), 2715 (1968) and Kalck, P., et al., *J. Organomet. Chem*, 24, 445 (1970), respectively incorporated herein by reference. Examples 10 to 22 describe the use of these catalysts and catalyst precursors in hydrogenation and hydrosilylation processes. Examples 23 to 26 describe the preparation of organometallic complexes of the invention. Examples 27 to 34 describe the use of these organometallic complexes as catalysts for catalytic processes.

Example 1

Synthesis of $CpMo(CO)_2(IMes)H$ from $CpMo(CO)_2(PPh_3)H$

For this example, $CpMo(CO)_2(PPh_3)H$ (480.0 mg, 1.000 mmol), IMes (306.0 mg, 1.000 mmol), and 10 mL of toluene were placed in a glass tube placed in a glove box. The glass tube was equipped with a teflon valve. The light yellow solids dissolved to produce a dark purple mother liquor. A new lightly colored precipitate formed almost immediately. The glass tube was heated at 95° C. for 3 hours. The product was recrystallized from toluene-hexanes (1:3) to yield 449 mg (86%) of pure $CpMo(CO)_2(IMes)H$ as light yellow crystals. The product had the following identification data:

$^1$H NMR (THF-$d_8$) δ 7.16 (s, 2H, =CH), 7.02 (s, 4H, m-H-Mes), 4.62 (s, 5H, Cp), 2.34 (s, 6H, p-Me-Mes), 2.09 (s, 12H, o-Me-Mes), −4.73 (s, 1H, MoH). $^{13}$C NMR (THF-$d_8$) δ 243.3 (d, $^2J_{CH}$=11 Hz, Mo—CO), 200.2 (d, $^2J_{CH}$=12 Hz, NCN), 139.5 (m, i-Mes), 139.2 (q, $^2J_{CH}$=6 Hz, p-Mes), 136.9 (q, $^2J_{CH}$=6 Hz, o-Mes), 130.0 (dm, $^1J_{CH}$=156 Hz, m-Mes), 124.3 (dd, $^1J_{CH}$=196 and $^2J_{CH}$=12 Hz, =CH), 89.0 (dp, $^1J_{CH}$=174 and $J_{CH}$=6 Hz, Cp), 21.2 (qt, $^1J_{CH}$=126 and $^3J_{CH}$=4 Hz, p-Me-Mes), 18.8 (qm, $^1J_{CH}$=128 Hz, o-Me-Mes). IR (THF-$d_8$) ν(CO)=1918 (vs) and 1843 (vs) $cm^{-1}$. IR (hexanes) ν(CO)=1930 (vs) and 1858 (vs) $cm^{-1}$. Analysis calculated for $C_{28}H_{30}N_2O_2Mo$: C, 64.37; H, 5.79; N, 5.36. Found: C, 64.13; H, 6.05; N, 5.34.

Example 2

Synthesis of cis-$CpW(CO)_2(IMes)H$ from $CpW(CO)_2(PPh_3)H$

In a glove box, $CpW(CO)_2(PPh_3)H$ (608 mg, 1.07 mmol), IMes (333 mg, 1.09 mmol), and 3 mL of toluene were placed in a glass tube equipped with a teflon valve. The yellow solids dissolved to produce a brown-red mother liquor. A new lightly colored precipitate formed within 10–20 minutes. The color faded slowly to yellow-gray, indicating completion of the reaction after two days at 23° C. The product was washed with 2×7 mL of hexanes and recrystallized from toluene-hexanes (1:1) to yield 568 mg (87%) of pure $CpW(CO)_2(IMes)H$ as light yellow crystals. The product was identified by comparison to an authentic sample of $CpW(CO)_2(IMes)H$, which was synthesized by an independent route. The product had the same identification data as set forth in Example 3 herein below.

Example 3

Synthesis of $CpW(CO)_2(IMes)H$ from $CpW(CO)_2(PMe_3)H$

In a glovebox, $CpW(CO)_2(PMe_3)H$ (346.0 mg, 0.900 mmol), IMes (275.0 mg, 0.900 mmol), and 1 mL of toluene were placed in a glass tube equipped with a teflon valve. The light yellow solids dissolved to produce a dark purple mother liquor. A new lightly colored precipitate formed almost immediately. The volatiles were removed in vacuo, and the residue was heated in dynamic vacuo for 10 minutes at 120° C. The product was recrystallized from toluene-hexanes (1:1) to yield 416 mg (76%) of pure $CpW(CO)_2(IMes)H$ as light yellow crystals with 0.5 equivalents of crystallization solvent ($C_6H_5CH_3$) Per W. The product had the following identification data:

$^1$H NMR ($C_6D_6$) δ 6.80 (s, 4H, m-H-Mes), 6.19 (s, 2H, =CH), 4.60 (s, 5H, Cp), 2.12 (s, 6H, p-Me-Mes), 2.10 (s, 12H, o-Me-Mes), −5.93 (s, $^1J_{WH}$=45 Hz, 1H, WH). $^1$H NMR (THF-$d_8$, −100° C.) δ 7.40 (s, 2H, =CH), 7.06 (s, 4H, m-H-Mes), 4.71 (s, 5H, Cp), 2.34 (s, 6H, p-Me-Mes), 2.12 (br s, 6H, o-Me-Mes), 2.01 (br s, 6H, o-Me-Mes), −6.43 (s, $^1J_{WH}$=45 Hz, 1H, WH). $^{13}$C NMR ($C_6D_6$) δ 238.1 (m, W—CO), 184.1 (d, $^2J_{CH}$=14.8 Hz, NCN), 139.1 (m, i-Mes), 138.9 (q, $^2J_{CH}$=6 Hz, p-Mes), 136.6 (q, $^2J_{CH}$=6 Hz, o-Mes), 129.9 (dm, $^1J_{CH}$=157 Hz, m-Mes), 122.9 (dd, $^1J_{CH}$=195 and $^2J_{CH}$=12 Hz, =CH), 87.4 (d quintet, $^1J_{CH}$=177 and $J_{CH}$=7 Hz, Cp), 21.4 (qt, $^1J_{CH}$=126 and $^3J_{CH}$=5 Hz, p-Me-Mes), 19.1 (qm, $^1J_{CH}$=127 Hz, o-Me-Mes). $^{13}C\{^1H\}$ NMR (THF-$d_8$, −100° C.) δ 247.4 (br s, W—CO), 232.3 (br s, W—CO), 181.5 (s, NCN), 139.4 (s, p-Mes or i-Mes), 138.9 (s, p-Mes or i-Mes), 137.1 (br s, o-Mes), 136.6 (br s, o-Mes), 129.8 (br s, m-Mes), 124.1 (br s, =CH), 88.0 (s, Cp), 21.3 (br s, p-Me-Mes), 19.4 (br s, o-Me-Mes), 18.9 (br s, o-Me-Mes). IR (toluene) ν(CO)=1915 (vs) and 1824 (vs) $cm^{-1}$. IR ($CD_2Cl_2$) ν(CO)=1906 (vs) and 1810 (vs) $cm^{-1}$. Analysis calculated for $C_{31.5}H_{34}N_2O_2W$ (with 0.5 equiv. of crystallization solvent, $C_6H_5CH_3$, per W): C, 57.63; H, 5.22; N, 4.27. Found: C, 57.52; H, 5.07; N, 4.14.

Example 4

Synthesis of $[CpMo(CO)_2(IMes)]^+[B(C_6F_5)_4]^-$ ·$0.5CH_3Ph$

For this example, $CpMo(CO)_2(IMes)H$ (52.4 mg, 0.100 mmol) was added slowly to a stirred solution of $Ph_3C^+B(C_6F_5)_4^-$ (96.6 mg, 0.105 mmol) in 5 mL of toluene in a glass tube contained in a glovebox. The tube was equipped with a teflon valve. A dark purple precipitate formed. The stirring was continued for 40 minutes. The bright yellow mother liquor was discarded, and the precipitate was washed with toluene until the washings were colorless (5×3 mL). The product was washed with hexanes (3×3 mL) and dried in vacuo to yield 112 mg (87%) of dark purple crystals of pure $CpMo(CO)_2(IMes)^+B(C_6F_5)_4^-$ with 0.5 equivalents of crystallization solvent ($C_6H_5CH_3$) per Mo. The product was insoluble in common non-coordinating NMR solvents. IR (Nujol) ν(CO)=1999 (vs) and 1905 (vs) $cm^{-1}$. Analysis Calculated for $C_{55.5}H_{33}BF_{20}N_2O_2Mo$ including 0.5 equivalents of crystallization solvent, $C_6H_5CH_3$, per Mo was: C, 53.47; H, 2.67; N, 2.25. We found the following: C, 53.18; H, 2.77; N, 2.43.

The identification data of the product in THF-$d_8$ for cis-$[CpMo(CO)_2(IMes)(THF\text{-}d_8)]^+[B(C_6F_5)_4]^-$ was as follows: $^1$H NMR (THF-$d_8$) δ 7.83 (s, 2H, =CH), 7.13 (s, 4H, m-H-Mes), 5.14 (s, 5H, Cp), 2.36 (s, 6H, p-Me-Mes), 2.11 (s, 12H, o-Me-Mes). $^{13}C\{^1H\}$ NMR (THF-$d_8$) δ 251 (m, Mo—CO), 187.3 (s, NCN), 149.3 (dm, $^1J_{CF}$=246 Hz, o-$C_6F_5$), 141.0 (br s, p-Mes or i-Mes), 139.2 (dm, $^1J_{CF}$=243 Hz, p-$C_6F_5$), 137.4 (br s, p-Mes or i-Mes), 137.2 (dm, $^1J_{CF}$=244 Hz, m-$C_6F_5$), 136.5 (br s, o-Mes), 130.3 (br s, m-Mes), 127.6 (br s, =CH), 125 (br m, i-$C_6F_5$), 96.9 (s, Cp), 21.0 (s, p-Me-Mes), 18.7 (br s, o-Me-Mes). $^{19}$F NMR (THF-$d_8$) δ−132.9 (d, 8F, $^3J_{FF}$=10 Hz, o-$C_6F_5$), −165.1 (t, 4F, $^3J_{FF}$=21 Hz, p-$C_6F_5$), −168.6 (t, 8F, $^3J_{FF}$=18 Hz, m-$C_6F_5$). IR (THF) ν (CO)=1977 (vs) and 1882 (vs) $cm^{-1}$.

Example 5

Synthesis of $[CpW(CO)_2(IMes)]^+[B(C_6F_5)_4]^-$ ·$CH_3Ph$

In a glovebox, $CpW(CO)_2(IMes)H$ (244.0 mg, 0.400 mmol) was added slowly to a stirred solution of $Ph_3C^+B(C_6F_5)_4^-$ (387.0 mg, 0.420 mmol) in 10 mL of toluene in a glass tube equipped with a teflon valve. A dark purple precipitate formed. The stirring was continued for 30 minutes. The bright yellow mother liquor was discarded, and the precipitate was washed with toluene until the washings were colorless (5×3 mL). The product was washed with hexanes (3×3 mL) and dried in vacuo to yield 490 mg (91%) of dark purple crystals of $CpW(CO)_2(IMes)^+B(C_6F_5)_4^-$ with 1 equivalent of crystallization solvent ($C_6H_5CH_3$) per W. The product was insoluble in common non-coordinating NMR solvents. IR (Nujol) ν(CO)=1980 (vs) and 1890 (vs) $cm^{-1}$. IR ($CF_3Ph$) ν(CO)=1983 (vs) and 1900 (vs) $cm^{-1}$. Analysis calculated for $C_{59}H_{37}BF_{20}N_2O_2W$ was: C, 51.33; H, 2.70; N, 2.03. We found the following: C, 51.24; H, 3.35; N, 2.02.

The identification data of the product in THF-$d_8$ for cis-$[CpW(CO)_2(IMes)(THF\text{-}d_8)]^+[B(C_6F_5)_4]^-$ was as follows: $^1$H NMR (THF-$d_8$, −30° C.) δ 7.99 and 7.87 (d, $^1J_{HH}$=2 Hz, 1H, =CH), 7.26, 7.19, 7.16, and 7.03 (s, 1H, m-H-Mes), 5.36 (s, 5H, Cp), 2.41, 2.31, 2.30, 2.23, 2.14, and 2.02 (s, 3H, p-Me-Mes and o-Me-Mes). $^{13}C\{^1H\}$ NMR (THF-$d_8$, −40° C.) δ 247.1 and 246.2 (s, W—CO), 179.6 (s, NCN), 149.0 (br d, $^1J_{CF}$=240 Hz, o-$C_6F_5$), 141.3 and 140.0 (s, p-Mes or i-Mes), 139.1 (dm, $^1J_{CF}$=242 Hz, p-$C_6F_5$), 137.9 (s, p-Mes or i-Mes), 137.0 (dm, $^1J_{CF}$=244 Hz, m-$C_6F_5$), 137.5, 136.7, 136.5, and 135.8 (s, o-Mes), 130.7, 130.3, 130.2, and 129.4 (s, m-Mes), 128.4 and 126.6 (br s, =CH), 125 (br m, i-$C_6F_5$), 95.4 (s, Cp), 21.1 and 21.0 (s, p-Me-Mes), 19.7, 18.9, 18.7, and 18.6 (s, o-Me-Mes). $^{19}$F NMR (THF-$d_8$, −30° C.) δ−133.5 (d, 8F, $^3J_{FF}$=11 Hz, o-$C_6F_5$),−164.9 (t, 4F, $^3J_{FF}$=21 Hz, p-$C_6F_5$), −168.5 (t, 8F, $^3J_{FF}$=18 Hz, m-$C_6F_5$). IR (THF-$d_8$) ν(CO)=1962 (vs) and 1859 (vs) $cm^{-1}$.

Example 6

Synthesis of $[CpW(CO)_2(IMes)(H)_2]^+[B(C_6F_5)_4]^-$

In a glovebox, $[CpW(CO)_2(IMes)(CH_3Ph)]^+[B(C_6F_5)_4]^-$ (70 mg, 0.051 mmol) was placed in an NMR tube equipped with a teflon valve. The tube was taken out of the glovebox, and THF-$d_8$ was vacuum transferred into the tube, producing a dark purple solution. The tube was then filled with about 1.1 atm $H_2$ at −196° C., sealed, and warmed to room temperature. It was shaken for 3 minutes at room temperature and used for low temperature NMR measurements. The sample was found to contain $[CpW(CO)_2(IMes)(THF\text{-}d_8)]^+[B(C_6F_5)_4]^-$ and two isomers of $[CpW(CO)_2(IMes)(H)_2]^+[B(C_6F_5)_4]^-$. The identification data of these isomers was as follows:

Major isomer (about 85 mole %). $^1$H NMR ($C_6D_6$) δ 6.74 (s, 4H, m-H-Mes), 6.08 (s, 2H, =CH), 4.14 (s, 5H, Cp), 2.13 (s, 6H, p-Me-Mes), 1.62 (s, 12H, o-Me-Mes), −1.11 (br s, 2H, WH). $^1$H NMR (THF-$d_8$, −30° C.) δ 7.82 (s, 2H, =CH), 7.17 (s, 4H, m-H-Mes), 5.46 (s, 5H, Cp), 2.37 (s, 6H, p-Me-Mes), 2.06 (s, 12H, o-Me-Mes), −0.7 (br s, $ν_{1/2}$=1400 Hz, 2H, WH). $^1$H NMR (THF-$d_8$, −100° C.) δ 7.95 (s, 2H, =CH), 7.19 (s, 4H, m-H-Mes), 5.59 (s, 5H, Cp), 2.38 (s, 6H, p-Me-Mes), 2.07 (s, 12H, o-Me-Mes), 1.19 (br s, $ν_{1/2}$=13 Hz, 1H, WH), −2.97 (~br d, $ν_{1/2}$=12 Hz, $^1J_{HH}$=3 Hz, $^1J_{HW}$=34 Hz, 1H, WH). $^{13}C\{^1H\}$ NMR (THF-$d_8$, −100° C.) δ 205.2 and 203.1 (s, W—CO), 160.7 (s, NCN), 148.8 (br d, $^1J_{CF}$=242 Hz, o-$C_6F_5$), 141.0 (br s, p-Mes or i-Mes), 139.0 (dm, $^1J_{CF}$=242 Hz, p-$C_6F_5$), 138.5 (s, p-Mes or i-Mes), 137.0 (dm, $^1J_{CF}$=247 Hz, m-$C_6F_5$), 136.4 (br s, o-Mes), 130.6 and 130.5 (s, m-Mes), 127.9 (br s, =CH), 124.5 (br m, i-$C_6F_5$), 88.6 (s, Cp), 21.2 (s, p-Me-Mes), 18.7 and 18.3 (s, o-Me-Mes). $^{19}$F NMR (THF-$d_8$, −30° C.) δ−133.5 (d, 8F, $^3J_{FF}$=11 Hz, o-$C_6F_5$), −164.9 (t, 4F, $^3J_{FF}$=21 Hz, p-$C_6F_5$), −168.5 (t, 8F, $^3J_{FF}$=18 Hz, m-$C_6F_5$). IR (THF-$d_8$) ν(CO)=2063 (vs) and 2007 (vs) $cm^{-1}$.

Minor isomer (about 15 mole %). $^1$H NMR ($C_6D_6$) δ 6.57 (br s, 4H, m-H-Mes), 5.97 (br s, 2H, =CH), 3.96 (br s, 5H, Cp), 1.97 (br s, 6H, p-Me-Mes), 1.44 (br s, 12H, o-Me-Mes), −1.25 (br s, 2H, $WH_2$). $^1$H NMR (THF-$d_8$, −30° C.) δ 7.76 (br s, 2H, =CH), 5.28 (s, 5H, Cp).

Example 7

Synthesis of $[CpW(CO)_2(IMes)(Et_2C{=}O)]^+[B(C_6F_5)_4]^-$

In a glovebox $[CpW(CO)_2(IMes)(CH_3Ph)]^+[B(C_6F_5)_4]^-$ (53 mg, 0.038 mmol) and 3-pentanone (300 μL, 2.83 mmol) were mixed to produce a dark purple solution and placed in an NMR tube equipped with a teflon valve. The volatiles were removed in vacuo, and the purple crystalline material was identified as $[CpW(CO)_2(IMes)(Et_2C{=}O)]^+[B(C_6F_5)_4]^-$. The identification data for this product was as follows:

$^1$H NMR ($C_6D_6$) δ 6.6 (br s, 4H, m-H-Mes), 6.10 (s, 2H, =CH), 4.49 (s, 5H, Cp), 2.08 (s, 6H, p-Me-Mes), 1.9 (br s, 4H, $CH_3CH_2$), 1.70 (br s, 12H, o-Me-Mes), 0.72 (br s, 6H, $CH_3CH_2$). $^1$H NMR ($Et_2C{=}O$ and a sealed capillary of $CD_2Cl_2$ for lock, −10° C.) δ 8.60 (s, 2H, =CH), 7.85 and 7.75 (br s, 4H, m-H-Mes), 5.98 (s, 5H, Cp), 2.71 (br s, 12H, o-Me-Mes), resonances of p-Me-Mes and Et presumably obscured by solvent. $^{13}C\{^1H\}$ NMR (liquid clathrate, $C_6D_6$) δ 244.4 (s, W—CO), 239 (br s, $Et_2C{=}O$), 177 (br s, NCN), 149.4 (dm, $^1J_{CF}$=244 Hz, o-$C_6F_5$), 141.1 (s, p-Mes or i-Mes; other resonance presumably obscured by signals around 138), 139.2 (dm, $^1J_{CF}$=246 Hz, p-$C_6F_5$), 137.3 (dm, $^1J_{CF}$=246 Hz, m-$C_6F_5$), 136.1 (bs s, o-Mes), m-Mes and =CH obscured by solvent at 130–127, 125.4 (br m, i-$C_6F_5$), 97 (br s, Cp), 36.6 (br s, $CH_3CH_2$), 20.9 (s, p-Me-Mes), 18.0 (br s, o-Me-Mes), 8 (br s, $CH_3CH_2$). $^{13}C\{^1H\}$ NMR ($Et_2C{=}O$ and a sealed capillary of $CD_2Cl_2$ for lock, −30° C.) δ 248.1 and 246.4 (s, W—CO), 241.1 (s, $Et_2C{=}O$), 177.4 (s, NCN), 148.7 (dm, $^1J_{CF}$=244 Hz, o-$C_6F_5$), 140.8 (br s, p-Mes or i-Mes), 138.7 (dm, $^1J_{CF}$=247 Hz, p-$C_6F_5$), 136.9 (s, p-Mes or i-Mes), 136.7 (dm, $^1J_{CF}$=247 Hz, m-$C_6F_5$), 136.7 (s, o-Mes), 130.2 (s, m-Mes), 128 and 126 (br s, =CH), 124.6 (br m, i-$C_6F_5$), 96.0 (s, Cp), 37.8 (s, $CH_3CH_2$), 21.0 (s, p-Me-Mes), 18.8, 18.6, and 17.9 (s, o-Me-Mes), 8.9 (s, $CH_3CH_2$). $^{19}$F NMR δ ($Et_2C{=}O$ and a sealed capillary of $CD_2Cl_2$ for lock, −30° C.)−133.3 (dm, 8F, $^3J_{FF}$=11 Hz, o-$C_6F_5$), −164.3 (tm, 4F, $^3J_{FF}$=21 Hz, p-$C_6F_5$), −168.2 (tm, 8F, $^3J_{FF}$=17 Hz, m-$C_6F_5$). IR (THF) ν(CO)=1963 (vs) and 1863 (vs), ν($Et_2C{=}O$)=1718 (w) $cm^{-1}$. UV(toluene) $λ_{max}$=498 nm (ε=1·$10^3$ L·$mol^{-1}$·$cm^{-1}$).

Example 8

Synthesis of $[CpW(CO)_2(IMes)(SiEt_3)H]^+[B(C_6F_5)_4]^-$

In a glovebox, a solution of $HSiEt_3$ (16 μL, 0.10 mmol) in 0.5 mL of diethyl ether was added to [CpW(CO)_2(IMes)

$(CH_3Ph)]^+[B(C_6F_5)_4]^-$ (69 mg, 0.050 mmol). The sample was stirred for 10 minutes, and the volatiles were removed in vacuo to produce $[CpW(CO)_2(IMes)(SiEt_3)H]^+$ $[B(C_6F_5)_4]^-$ as a brown-yellow product. Two isomers were isolated and their identification data is set forth below.

Major isomer (about 70 mole % at 25° C.): $^1H$ NMR ($C_6D_6$) δ 6.74 and 6.69 (s, 2H, m-H-Mes), 6.12 (s, 2H, =CH), 4.64 (s, 5H, Cp), 2.11 (s, 6H, p-Me-Mes), 1.78 and 1.71 (s, 6H, o-Me-Mes), 0.67 (t, 9H, $^3J_{HH}$=8 Hz, $CH_3CH_2$), 0.31 (dq, 6H, $^3J_{HH}$=2 and 8 Hz, $CH_3CH_2$), −2.60 (s, 1H, $^1J_{HW}$=36 Hz, WH). $^{13}C\{^1H\}$ NMR (liquid clathrate, $C_6D_6$) δ 217.2 (br s, CO), 172.3 (s, $^1J_{HW}$=134 Hz, NCN), 149.5 (br d, $^1J_{CF}$=244 Hz, o-$C_6F_5$), 141.0 (s, p-Mes or i-Mes), 139.3 (dm, $^1J_{CF}$=250 Hz, p-$C_6F_5$), 137.4 (dm, $^1J_{CF}$=250 Hz, m-$C_6F_5$), 136.9 (s, p-Mes or i-Mes), 135.7 (s, o-Mes), 130.4 (br s, m-Mes), 125.5 (br m, i-$C_6F_5$), 125.4 (s, =CH), 92.2 (s, Cp), 21.1 (s, p-Me-Mes), 18.1 (br s, o-Me-Mes), 5.9 (s, $CH_3CH_2$), 4.7 (s, $^1J_{CSi}$=59 Hz, $CH_3CH_2$). $^{19}F$ NMR δ ($C_6D_6$) −133.1 (br s, 8F, o-$C_6F_5$), −164.1 (t, 4F, $^3J_{FF}$=20 Hz, p-$C_6F_5$), −167.9 (br s, 8F, m-$C_6F_5$). $^{29}Si$ NMR δ ($C_6D_6$) 43.2 (s, W—Si). IR (THF-$d_8$) ν(CO)=1979 (vs) and 1948 (vs) $cm^{-1}$.

Minor isomer (about 30 mole % at 25° C.): $^1H$ NMR ($C_6D_6$) δ 6.60 and 6.56 (br s, 2H, m-H-Mes), 6.05 (br s, 2H, =CH), 4.46 (br s, 5H, Cp), 1.99 (br s, 6H, p-Me-Mes), 1.63 and 1.56 (br s, 6H, o-Me-Mes), 0.54 (br t, 9H, $^3J_{HH}$=8 Hz, $CH_3CH_2$), 0.20 (br q, 6H, $^3J_{HH}$=8 Hz, $CH_3CH_2$), −2.69 (s, 1H, $^1J_{HW}$=36 Hz, WH).

Example 9

Catalytic Hydrogenation of 3-pentanone

In this example, $CpW(CO)_2(IMes)^+B(C_6F_5)_4^-$ (26.5 mg, 0.019 mmol) as prepared in Example 5 and 3-pentanone (600 μL, 5.65 mmol) were placed in a glass tube (125 mL capacity) equipped with a teflon valve and the tube was placed in a glove box. The solution was freeze-pump-thawed, frozen again, and the entire tube was submersed in liquid nitrogen. The tube was then filled with about 1.1 atm $H_2$, sealed, and warmed to room temperature. As a result the tube contained 20.1 mmol of $H_2$ at about 4.1 atm and room temperature. The reaction was carried out at 50° C. in a constant-temperature bath. Aliquots were removed by cooling the tube to 77° K., evacuating $H_2$, refilling the tube with Ar, and taking it into the glovebox. After removal of an aliquot of about 60 μL, the tube was again freeze-pump-thawed, then filled with 1.1 atm $H_2$ at 77K and re-sealed. The aliquot was diluted in 500 μL of each $C_6D_6$, and the solution was analyzed by $^1H$ NMR. After 1 hour, TON(total) was 1.0 of which TON(ether) was 0. After 23 hours, TON (total) was 15.1, of which TON(ether) was 0.4. After 6.8 days, TON(total) was 29.9, of which TON(ether) was 0.7, representing a total of 10% conversion of the initial ketone.

Example 10

Catalytic Hydrogenation of 3-pentanone

This example is similar to Example 9 above, except that the reaction was carried out at 23° C. $CpW(CO)_2(IMes)^+B(C_6F_5)_4^-$ (13.3 mg, 0.010 mmol) and 3-pentanone (300 μL, 2.83 mmol) were used according to the same procedure as described for Example 6. After 24 hours, TON(total) was 2.1, of which TON(ether) was 0. After 9.9 days, TON(total) was 10.0, of which TON(ether) was 0, representing a total of 3% conversion of the initial ketone.

Example 11

Catalytic Hydrogenation of 3-pentanone

This example is similar to Example 10, except that it was carried out at high pressure of $H_2$ of about 800 psi. $CpW(CO)_2(IMes)^+B(C_6F_5)_4^-$ (53.0 mg, 0.040 mmol) and 3-pentanone (1.20 mL, 11.3 mmol) were placed in a stainless steel high pressure vessel in a glove box. The vessel was sealed and removed from the glovebox. $H_2$ was added at 800 psi, and the reaction was carried out at room temperature. Prior to removal of each sample for analysis, the bottom of the high pressure vessel was cooled at 77° K., and the pressure was slowly vented. The sample for NMR analysis was taken in a glove box under an argon atmosphere, and the vessel was resealed and repressurized with $H_2$. After 24 hours, TON(total) was 7.8, of which TON(ether) was 0.2. After 10.0 days, TON(total) was 86, of which TON(ether) was 6, representing a total of 29% conversion of the initial ketone.

Example 12

Catalytic Hydrogenation of 3-pentanone

This example is similar to Example 11 (800 psi of $H_2$), except that the reaction was carried out at 50° C. $CpW(CO)_2(IMes)^+B(C_6F_5)_4^-$ (13.3 mg, 0.010 mmol) and 3-pentanone (300 μL, 2.83 mmol) were placed in a stainless steel high pressure vessel in a glove box. $H_2$ was added at 800 psi initial at room temperature, and the reaction as carried out at 50° C. Prior to removal of each sample for analysis, the bottom of the high pressure was cooled at 77° K., and the pressure was slowly vented. After 24 hours, TON(total) was 15.9, of which TON(ether) was 3.8. After 7.0 days, TON (total) was 60.9, of which TON(ether) was 12.6, representing a total of 21% conversion of the initial ketone.

Example 13

Catalytic Hydrogenation of 3-pentanone

This example is similar to Example 9 (50° C.), except that a Mo-based catalyst was used instead of W. $CpMo(CO)_2(IMes)^+B(C_6F_5)_4^-$ (13.3 mg, 0.010 mmol) prepared according to Example 4 and 3-pentanone (300 μL, 2.83 mmol) were used for the same procedure as described for Example 6. After 24 hours, TON(total) was 0.8, of which TON(ether) was 0. After 9.9 days, TON(total) was 1.0, of which TON (ether) was 0, representing a total of 0.3% conversion of the initial ketone.

Example 14

Catalytic Hydrogenation of 3-pentanone

This example is similar to Example 10 (23° C.), except that Mo-based catalyst was used instead of W. $CpMo(CO)_2(IMes)^+B(C_6F_5)_4^-$ (13.3 mg, 0.010 mmol) prepared according to Example 4 and 3-pentanone (300 μL, 2.83 mmol) were used according to the same procedure as described for Example 7. After 24 hours, TON(total) was 0.9, of which TON(ether) was 0. After 9.9 days, TON(total) was 0.9, of which TON(ether) was 0, representing a total of 0.3% conversion of the initial ketone.

Example 15

Catalytic Hydrosilylation of 3-pentanone

In a glove box $CpW(CO)_2(IMes)^+B(C_6F_5)_4^-$ (4.1 mg, 0.003 mmol), prepared according to Example 5 and 3-pentanone (159 μL, 1.50 mmol), and $HSiEt_3$ (288 μL, 1.80 mmol) were placed in an NMR tube equipped with a teflon valve. Two sealed capillaries with $C_6D_6$ were placed in the same tube for NMR lock purpose. The tube was shaken to mix the ingredients producing a deep purple homogeneous solution. The color faded to light purple within 2 minutes. The reaction was carried out at 23° C. The progress of the reaction was periodically monitored by $^{1}H$ NMR. At high conversions polarity of the medium drastically decreased. A light purple precipitate was formed and the solution turned colorless. After 15 minutes, TON(alkoxysilane) was 373, TON(ether)=13, and TON(2-pentene) was 16. After 1 hour, TON(alkoxysilane)=466, TON(ether) was 14, and TON(2-pentene) was 21, representing a total of 100% conversion of the initial ketone. The liquid was decanted, and the solid catalyst was re-used without any significant loss of activity or selectivity. The recycled active catalyst was identified by NMR as a mixture of $CpW(CO)_2(IMes)(SiEt_3)H]^+$ $[B(C_6F_5)_4]^-$ and $CpW(CO)_2(IMes)(H)_2]^+[B(C_6F_5)_4]^-$.

Example 16

Catalytic Hydrosilylation of 3-Acetophenone

This example is similar to Example 15, except that acetophenone was used instead of 3-pentanone. In a glove box, $CpW(CO)_2(IMes)^+B(C_6F_5)_4^-$ (4.1 mg, 0.003 mmol), acetophenone (175 μL, 1.50 mmol), $HSiEt_3$ (288 μL, 1.80 mmol), and two sealed capillaries with $C_6D_6$ were placed in an NMR tube equipped with a teflon valve. The reaction was carried out at 23° C. The solution remained homogeneous, and the color gradually changed from purple to light yellow. After 15 minutes, TON(alkoxysilane) was 26 and TON (ethylbenzene) was 0. After 23 hours, TON(alkoxysilane) was 446, TON(ethylbenzene) was 11, representing a total of 100% conversion of the initial ketone.

The same procedures as described in Examples 15 and 16 above were used for hydrosilylation of other aromatic ketones. The results are presented in Table 3 below.

TABLE 3

Hydrosilylation of Carbonyl Compounds by W and Mo Catalysts

| # | catalyst[a] (T, ° C.) | silane | silane/ substrate ratio | substrate | products | initial TOF[b] $h^{-1}$ | total TON[c] (yield, %) | time hours |
|---|---|---|---|---|---|---|---|---|
| 1 | W (23) | $HSiEt_3$ | 1.2 | 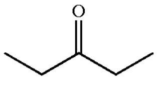 | 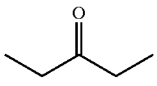 | 1490 | 466 (93.2) | 1 |
| | | | | | 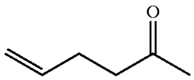 | 62 | 21 (4.1) | |
| | | | | | 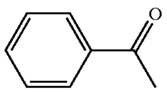 | 52 | 14 (2.7) | |
| 2 | Mo (23) | $HSiEt_3$ | 1.2 | 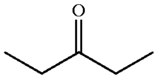 | 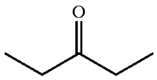 | 10 | 29 (5.8) | 25 |
| | | | | | 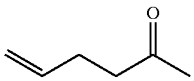 | n. d.[d] | 1 (0.2) | |
| | | | | | 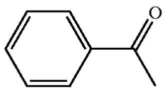 | 0 | 0(0) | |
| 3 | Mo (53) | $HSiEt_3$ | 1.2 | 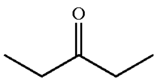 | 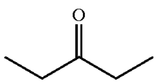 | 10 | 12 (2.3) | 1.2 |
| | | | | | 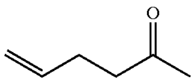 | n. d. | 1 (0.2) | |
| | | | | | 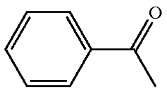 | 0 | 0 (0) | |
| 4 | W (23) | $HSiEt_3$ | 1.2 | 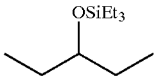 | 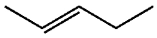 | 104 | 446 (89.1) (89.1) | 23 |

TABLE 3-continued

Hydrosilylation of Carbonyl Compounds by W and Mo Catalysts

| # | catalyst[a] (T, ° C.) | silane | silane/ substrate ratio | substrate | products | initial TOF[b] $h^{-1}$ | total TON[c] (yield, %) | time hours |
|---|---|---|---|---|---|---|---|---|
| | | | | | 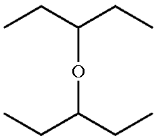 | n. d. | 11 (2.1) | |
| 5 | Mo (23) | $HSiEt_3$ | 1.2 | 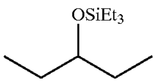 | 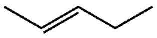 | 1 | 12 (2.4) | 23 |
| | | | | | 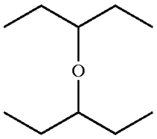 | 0 | 0 (0) | |
| 6 | Mo (53) | $HSiEt_3$ | 1.2 | 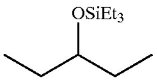 | 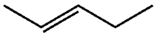 | 11 | 111 (22.1) | 23 |
| | | | | | 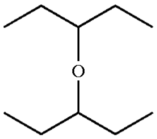 | 0 | 0 (0) | |
| 7 | W (23) | $HSiEt_3$ | 1.2 | 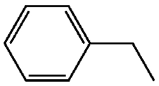 | 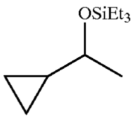 | 66 | 4494 (98.7) | 21 |
| | | | | | 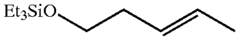 | 0 | 2 (0.4) | |
| 8 | W (23) | $HSiEt_3$ | 2.3 | 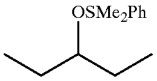 | $EtOSiEt_3$ | 173 | 468 (93.6) | 26 |
| | | | | | $Et_2O$ | n. d. | 30 (5.9) | |

[a]W = $CpW(CO)_2(IMes)^+B(C_6F_5)_4^-$, Mo = $CpMo(CO)_2(IMes)^+B(C_6F_5)_4^-$
[b]initial TOF is an average turnover frequency for a given product, measured within the first 15–20 minutes of the reaction.
[c]total TON is a total number of turnovers for a given product, measured at the end of the reaction. The end of the reaction is defined either by complete conversion of the substrate (organic carbonyl compound) or by complete decomposition of the catalysts to unreactive species.
[d]n. d.—not determined

Example 17

Catalytic Hydrosilylation of an Ester

This example is similar to Example 15, except that hydrosilylation of an ester required 2 equivalents of $HSiEt_3$ per 1 equivalent of substrate. In a glove box, $CpW(CO)_2(IMes)^+B(C_6F_5)_4^-$ (2.8 mg, 0.002 mmol), ethyl acetate (98 μL, 1.00 mmol), $HSiEt_3$ (352 μL, 2.20 mmol), and two sealed capillaries with $C_6D_6$ were placed in an NMR tube equipped with a teflon valve. The reaction was carried out at 23° C. At high conversions the polarity of the medium drastically decreased. A light purple precipitate was formed and solution turned colorless. After 18 minutes, TON (alkoxysilane) was 52 and TON(ether) was 0. After 26 hours, TON(alkoxysilane) was 468 and TON(ether) was 30, representing a total of 100% conversion of the initial ester.

Example 18

Catalytic Hydrosilylation of an Aldehyde

This example is similar to Example 15, except that 1-heptanal was used instead of 3-pentanone. In a glove box $CpW(CO)_2(IMes)^+B(C_6F_5)_4^-$ (4.1 mg, 0.003 mmol), 1-heptanal (209 μL, 1.50 mmol), $HSiEt_3$ (288 μL, 1.80 mmol), and two sealed capillaries with $C_6D_6$ were placed in an NMR tube equipped with a teflon valve. The reaction was carried out at 23° C. At high conversions polarity of the media drastically decreased. A light yellow precipitate was formed and solution turned light yellow. After 15 minutes, TON(alkoxysilane) was 248 and TON(ether) was 96. After 1.5 hours, TON(alkoxysilane)=295 and TON(ether)=105, representing a total of 81% yield and a 100% consumption of the initial aldehyde.

Example 19

Catalytic Hydrosilylation of $Et_2C{=}O$ with $HSiMe_2Ph$

In a glovebox $[CpW(CO)_2(IMes)]^+[B(C_6F_5)_4]^-.CH_3Ph$ (4 mg, 0.003 mmol), as prepared in Example 5, $Et_2C{=}O$ (1.50 mmol, 159 μL), and $HSiMe_2Ph$ (280 μL, 1.80 mmol) were placed in an NMR tube equipped with a Teflon valve. Two sealed capillaries with $C_6D_6$ were placed in the tube for the purpose of NMR lock. The tube was shaken to mix the ingredients, producing a yellow homogeneous solution. The reaction was carried out at room temperature (about 23° C.) and reached completion before the first NMR measurement, in about less then 15 min. The mixture appeared deceptively homogeneous, but small amount of brown oil precipitated after an overnight period.

Example 20

Catalytic Hydrosilylation of Aromatic Ketones

In a glove box $[CpW(CO)_2(IMes)]^+[B(C_6F_5)_4]^-.CH_3Ph$ (4 mg, 0.003 mmol), as prepared in Example 5, aromatic ketone (1.50 mmol, 175 μL in case of PhC(O)Me or 182 μL in case of p-F—$C_6H_4C(O)CH_3$), $HSiEt_3$ (288 μL, 1.80 mmol), and two sealed capillaries with $C_6D_6$ were placed in an NMR tube equipped with a Teflon valve. The reaction was carried out either at room temperature (about 23° C.) or at 53° C. in a constant-temperature bath. The progress of the reaction was periodically monitored by $^1H$ NMR. The color gradually changed from purple to light brown, and small amount of brown oily precipitate was formed.

Example 21

Composition of the Liquid Clathrate Formed in the Hydrosilylation of PhC(O)Me

In a glove box $[CpW(CO)_2(IMes)]^+[B(C_6F_5)_4]^-.CH_3Ph$ (40 mg, 0.030 mmol), as prepared in Example 5, PhC(O)Me (1.50 mmol, 175 μL), and $HSiEt_3$ (288 μL, 1.80 mmol) were mixed and placed in a Pasteur pipet sealed at the narrow end. The pipet was capped with a rubber septa and was left at room temperature (about 23° C.) inside the glove-box. The color quickly changed from purple to light brown, and brown oily precipitate was formed in the narrow part of the pipet within about 30 minutes. The oil proved to be viscous and difficult to transfer from one vessel to another, and the use of a sealed pipet was a convenient way to deliver the oil to the narrow part of the pipet. The system was allowed to equilibrate for another 2 h, and the top liquid phase was removed. The bottom section of the pipet was cut off yielding a capillary filled with brown oil. This capillary and two sealed capillaries with $C_6D_6$ were loaded in an NMR tube equipped with a Teflon valve. Note that constraining the oil to a narrow capillary was done primarily for the purpose of better magnetic field homogeneity throughout the sample and therefore, better resolution in the NMR spectra. The composition of the oil was determined by $^1H$ NMR spectroscopy to have about 3.4 equivalents of $PhCH(CH_3)OSiEt_3$ per $[CpW(CO)_2(IMes)H_2]^+[B(C_6F_5)_4]^-$.). The product had the following identification data: $^1H$ NMR (neat) δ 7.0 and 6.9 (overlapping br s, $v_{1/2}$~150 Hz, 5H of Ph and 6H of IMes), 4.6 (br s, $v_{1/2}$=150 Hz, 1H of PhCH and 5H of Cp), 1.9 and 1.7 (overlapping br s, $v_{1/2}$~300 Hz, 18H, IMes), 1.1 (br s, $v_{1/2}$~150 Hz, 3H, MeCHOSi), 0.7 (br s, $v_{1/2}$~150 Hz, 9H, $MeCH_2Si$), 0.3 (br s, $v_{1/2}$~150 Hz, 6H, $MeCH_2Si$), −1.1 (br s, $v_{1/2}$~200 Hz, 2H, $WH_2$.

Example 22

Catalytic Hydrosilylation of Ethyl Acetate

In a glove box $[CpW(CO)_2(IMes)]^+[B(C_6F_5)_4]^-\cdot CH_3Ph$ (2.8 mg, 0.002 mmol), ethyl acetate (98 μL, 1.00 mmol), $HSiEt_3$ (352 μL, 2.20 mmol), and two sealed capillaries with $C_6D_6$ were placed in an NMR tube equipped with a Teflon valve. The reaction was carried out at room temperature (~23° C.). At high conversions polarity of the medium drastically decreased and a purple oil separated from a very light purple solution. When all carbonyl substrate was consumed, the solution turned colorless and the oil changed color from purple to yellow and gradually turned into a solid or a semi-solid.

Characterization of products of hydrosilylation. The products were characterized by GC-MS, $^1H$, and $^{13}C$ NMR. Identification data of $Et_2CHOSiEt_3$, $EtOSiEt_3$, and $PhCH(CH_3)OSiEt_3$ is set forth below. The products had the following identification data:

$Et_2CHOSiEt_3$: $^1H$ NMR ($CDCl_3$) δ 3.53 (quintet, 1H, $^3J_{HH}$=6 Hz, $Et_2CH$), 1.47 (m, 4H, $CH_2CH$), 0.98 (t, 9H, $^3J_{HH}$=8 Hz, $CH_3CH_2Si$), 0.89 (t, 6H, $^3J_{HH}$=8 Hz, $CH_3CH_2CH$), 0.62 (q, 6H, $^3J_{HH}$=8 Hz, $CH_3CH_2Si$). $^1H$ NMR ($C_6D_6$) δ 3.48 (quintet, 1H, $^3J_{HH}$=6 Hz, $Et_2CH$), 1.44 (m, 4H, $CH_2CH$), 1.01 (t, 9H, $^3J_{HH}$=8 Hz, $CH_3CH_2Si$), 0.87 (t, 6H, $^3J_{HH}$=8 Hz, $CH_3CH_2CH$), 0.60 (q, 6H, $^3J_{HH}$=8 Hz, $CH_3CH_2Si$). $^{13}C$ NMR ($CDCl_3$) δ 75.0 (s, $Et_2CH$), 29.6 (s, $CH_2CH$), 9.9 (s, $CH_3CH_2CH$), 7.1 (s, $CH_3CH_2Si$), 5.3 (s, $^1J_{CSi}$=59 Hz, $CH_3CH_2Si$). MS, m/z 201 ($(M-H)^+$, 1), 173 (95), 103 (100), 75 (80).

$(Et_2CH)_2O$: $^1H$ NMR ($CDCl_3$) δ 3.16 (quintet, 1H, $^3J_{HH}$=6 Hz, $Et_2CH$), 1.47 (m, 4H, $CH_2CH$), 0.89 (t, 6H, $^3J_{HH}$=8 Hz, $CH_3CH_2CH$). $^1H$ NMR ($C_6D_6$) δ 3.04 (quintet, 1H, $^3J_{HH}$=6 Hz, $Et_2CH$), 1.44 (m, 4H, $CH_2CH$), 0.87 (t, 6H, $^3J_{HH}$=8 Hz, $CH_3CH_2CH$). $^{13}C$ NMR ($CDCl_3$) δ 79.7 (s, $Et_2CH$), 26.6 (s, $CH_2CH$), 9.9 (s, $CH_3CH_2CH$). MS, m/z 129 ($(M-Et)^+$, 20), 71 (40), 59 (100).

$Et_2CHOSiMe_2Ph$: $^1H$ NMR ($CDCl_3$) δ 7.66 (m, 2H, o-Ph), 7.41 (m, 3H, m-Ph and p-Ph), 3.60 (quintet, 1H, $^3J_{HH}$=6 Hz, $Et_2CH$), 1.50 (m, 4H, $CH_2CH$), 0.90 (t, 6H, $^3J_{HH}$=7 Hz, $CH_3CH_2CH$), 0.45 (s, 6H, $CH_3Si$). $^1H$ NMR ($C_6D_6$) δ 7.60 (m, 2H, o-Ph), 7.27 (m, 3H, m-Ph and p-Ph), 3.50 (quintet, 1H, $^3J_{HH}$=6 Hz, $Et_2CH$), 1.46 (m, 4H, $CH_2CH$), 0.88 (t, 6H, $^3J_{HH}$=7 Hz, $CH_3CH_2CH$), 0.39 (s, 6H, $CH_3Si$). $^{13}C$ NMR ($CDCl_3$) δ 138.9 (s, i-Ph), 133.8 (s, o-Ph), 129.6 (s, p-Ph), 127.9 (s, m-Ph), 75.6 (s, $Et_2CH$), 29.5 (s, $CH_2CH$), 10.0 (s, $CH_3CH_2CH$), −0.7 (s, $^1J_{CSi}$=61 Hz, $CH_3Si$). MS, m/z 221 ($(M-H)^+$, <0.1), 207 (5), 193 (40), 137 (60), 135 (100).

$CH_2{=}CH(CH_2)_2CH(Me)OSiEt_3$: $^1H$ NMR ($CDCl_3$) δ 5.80 (m, 1H, HC=), 4.99 (dq, 1H, $J_{HH}$=17 and 2 Hz, $H_2C$=), 4.92 (dm, 1H, $J_{HH}$=10 Hz, $H_2C$=), 3.80 (sextet, 1H, $^3J_{HH}$=6 Hz, SiOCH), 2.08 (m, 2H, $CH_2CH$=), 1.50 (m, 2H, $CH_2CH_2CH$=), 1.13 (d, $^3J_{HH}$=6 Hz, 3H, Me), 0.95 (t, 9H, $^3J_{HH}$=8 Hz, $CH_3CH_2Si$), 0.59 (q, 6H, $^3J_{HH}$=8 Hz, $CH_3CH_2Si$). $^{13}C$ NMR ($CDCl_3$) δ 139.0 (s, HC=), 114.4 (s, $H_2C$=), 68.1 (s, SiOCH), 39.2 and 30.3 (s, $CH_2$), 24.0 (s, Me), 7.1 (s, $CH_3CH_2Si$), 5.2 (s, $^1J_{CSi}$=59 Hz, $CH_3CH_2Si$). MS, m/z 213 ($(M-H)^+$, <0.1), 185 (40), 103 (100), 75 (60).

$PhCH(CH_3)OSiEt_3$: $^1H$ NMR ($CDCl_3$) δ 7.43 (m, 2H, Ph), 7.39 (m, 2H, Ph), 7.30 (m, 1H, Ph), 4.97 (q, 1H, $^3J_{HH}$=6 Hz, $CH_3CH$), 1.53 (d, 3H, $^3J_{HH}$=6 Hz, $CH_3CH$), 1.03 (t, 9H, $^3J_{HH}$=8 Hz, $CH_3CH_2Si$), 0.68 (dq, 6H, $^3J_{HH}$=4 and 8 Hz, $CH_3CH_2Si$). $^1H$ NMR ($C_6D_6$) δ 7.33 (m, 2H, Ph), 7.18 (m, 2H, Ph), 7.07 (m, 1H, Ph), 4.77 (q, 1H, $^3J_{HH}$=6 Hz, $CH_3CH$), 1.40 (d, 3H, $^3J_{HH}$=6 Hz, $CH_3CH$), 0.94 (t, 9H, $^3J_{HH}$=8 Hz, $CH_3CH_2Si$), 0.56 (dq, 6H, $^3J_{HH}$=4 and 8 Hz, $CH_3CH_2Si$). $^{13}C$ NMR ($CDCl_3$) δ 147.1 (s, i-Ph), 128.3 (s, o- or m-Ph), 127.0 (s, p-Ph), 125.4 (s, o- or m-Ph), 70.8 (s, $CHCH_3$), 27.5 (s, $CH_3CH$), 7.0 (s, $CH_3CH_2Si$), 5.1 (s, $^1J_{CSi}$=59 Hz, $CH_3CH_2Si$). MS spectrum matched with National Institute of Standards and Technology (NIST) database.

p-F—$C_6H_4$—$CH(CH_3)OSiEt_3$: $^1H$ NMR ($CDCl_3$) δ 7.39 (m, 2H, Ar), 7.05 (tt, 2H, $J_{HH}$=3 and 9 Hz, Ar), 4.95 (q, 1H, $^3J_{HH}$=6 Hz, $CH_3CH$), 1.50 (d, 3H, $^3J_{HH}$=6 Hz, $CH_3CH$), 1.02 (t, 9H, $^3J_{HH}$=8 Hz, $CH_3CH_2Si$), 0.67 (dq, 6H, $^3J_{HH}$=3 and 8 Hz, $CH_3CH_2Si$). $^1H$ NMR ($C_6D_6$) δ 7.10 (m, 2H, Ar), 6.82 (m, 2H, Ar), 4.66 (q, 1H, $^3J_{HH}$=6 Hz, $CH_3CH$), 1.30 (d, 3H, $^3J_{HH}$=6 Hz, $CH_3CH$), 0.93 (t, 9H, $^3J_{HH}$=8 Hz, $CH_3CH_2Si$), 0.53 (dq, 6H, $^3J_{HH}$=3 and 8 Hz, $CH_3CH_2Si$). $^{13}C$ NMR ($CDCl_3$) δ 162.1 (d, $^1J_{CF}$=244 Hz, Ar), 143.0 (d, $^4J_{CF}$=3 Hz, Ar), 126.9 (d, $^3J_{CF}$=8 Hz, Ar), 115.0 (d, $^2J_{CF}$=21 Hz, Ar), 70.3 (s, $CHCH_3$), 27.5 (s, $CH_3CH$), 6.9 (s, $CH_3CH_2Si$), 5.1 (s, $^1J_{CSi}$=59 Hz, $CH_3CH_2Si$). MS matched with NIST database.

$C_3H_5CH(CH_3)OSiEt_3$: $^1H$ NMR ($CDCl_3$) δ 3.10 (q, 1H, $^3J_{HH}$=6 Hz, $CH_3CH$), 1.08 (d, 3H, $^3J_{HH}$=6 Hz, $CH_3CH$), 0.82 (t, 9H, $^3J_{HH}$=8 Hz, $CH_3CH_2Si$), 0.72 (m, 1H, $CHCHCH_3$), 0.44 (q, 6H, $^3J_{HH}$=8 Hz, $CH_3CH_2Si$), 0.27 (m, 2H, $CH_2CH$), 0.12 (m, 1H, $CH_2CH$), −0.02 (m, 1H, $CH_2CH$). $^{13}C$ NMR ($CDCl_3$) δ 72.3 (s, $CH_3CH$), 24.0 (s, $CH_3CH$), 19.3 (s, $CHCHCH_3$), 7.0 (s, $CH_3CH_2Si$), 5.3 (s, $^1J_{CSi}$=59 Hz, $CH_3CH_2Si$), 3.3 (s, $CH_2CH$), 2.1 (s, $CH_2CH$). MS, m/z 171 ($(M-Et)^+$, 80), 143 (85), 103 (100), 75 (95).

$CH_3CH{=}CH(CH_2)_2OSiEt_3$: $^1H$ NMR ($CDCl_3$) δ 5.30 (m, 2H, =CH), 3.46 (t, 2H, $^3J_{HH}$=7 Hz, $CH_2O$), 2.07 (q, 2H, $^3J_{HH}$=7 Hz, $CH_2CH_2O$), 1.50 (d, 3H, $^3J_{HH}$=6 Hz, $CH_3CH$=), 0.79 (t, 9H, $^3J_{HH}$=8 Hz, $CH_3CH_2Si$), 0.38 (q, 6H, $^3J_{HH}$=8 Hz, $CH_3CH_2Si$). $^{13}C$ NMR ($CDCl_3$) δ 127:8 (s, =CH), 127.0 (s, =CH), 63.2 (s, $CH_2O$), 36.6 (s, $CH_2CH$—$_2$ O), 18.1 (s, $CH_3CH$=), 6.9 (s, $CH_3CH_2Si$), 4.7 (s, $^1J_{CSi}$=59 Hz, $CH_3CH_2Si$). MS, m/z 171 ($(M-Et)^+$, 100), 117 (90), 115 (70), 75 (75).

Example 23

Synthesis of $[(1,3\text{-}(C_6F_5C_6H_{12})_2C_5H_3]W(CO)_2(IMes)(H)_2]^+B(C_6F_5)_4^-$ In this example a disubstituted cyclopentadiene, 1,3-$(C_6F_5C_6H_{12})_2C_5H_4$, is prepared by a procedure described in Venier, C. G., et al, 1990, for the preparation of di-tert-butylcyclopendadiene, except that $I(CH_2)_6C_6F_5$ is used instead of tert-butyl bromide. Deprotonation of 1,3-$(C_6F_5C_6H_{12})_2C_5H_4$ with n-BuLi in hexane produces 1,3-$(C_6F_5C_6H_{12})_2C_5H_3Li$, which is then converted to $[(C_6F_5C_6H_{12})_2C_5H_3]W(CO)_3H$ using a procedure as described in Cheng, T. Y., et al. 1998, for the synthesis of $(C_5H_4CO_2CH_3)W(CO)_3H$. $[(C_6F_5C_6H_{12})_2C_5H_3]W(CO)_3H$ is converted to $[C_6F_5C_6H_{12})_2C_5H_3]W(CO)_2(PPh_3)H$ using a procedure described in Bainbridge, A., et al 1968. $[C_6F_5C_6H_{12})_2C_5H_3]W(CO)_2(PPh_3)H$ is then converted to $[(C_6F_5C_6H_{12})_2C_5H_3]W(CO)_2(IMes)H$ (IMes=1,3-bis(2,4,6-trimethylphenyl)-imidazol-2-ylidene) using a procedure described in Dioumaev, V. K. et al. 2003. Reaction of the tungsten metal hydride with $Ph_3C^+B(C_6F_5)_4^-$ produces $[(C_6F_5C_6H_{12})_2C_5H_3]W(CO)_2(IMes)^+B(C_6F_5)_4^-$ by a procedure as described in Dioumaev, V. K. et al., 2003.

$[(1,3\text{-}(C_6F_5C_6H_{12})_2C_5H_3]W(CO)_2(IMes)^+B(C_6F_5)_4^-$, as shown in formula VII is a clathrate enabled catalyst that can be used for hydrogenation or hydrosilylation of ketones.

VII

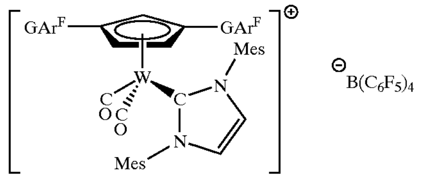

wherein $GAr^F$ is $(CH_2)_6C_6F_5$; and Mes is 2,4,6-trimethylphenyl.

Example 24

Synthesis of $(C_5H_5)W(CO)_2(Im^{ArC6ArF})^+B(C_6F_5)_4^-$

The synthesis of this complex is achieved by reacting commercially available 1,6-dibromohexane $[Br(CH_2)_6Br]$ with Mg metal in diethyl ether at room temperature for 6 hours to produce $BrMg(CH_2)_6MgBr$. An excess of $BrMg(CH_2)_6MgBr$ is coupled with commercially available $C_6F_5Br$ using a palladium-catalyzed cross-coupling reaction, followed by reaction with iodine, to generate $C_6F_5(CH_2)_6I$. Palladium-catalyzed cross couplings follow the procedure described in Diederich, F., et al., 1998 and can be accomplished either from the Grignard reagent as shown below in equation 3 and as described by Hayashi, T., et al., 1984, or through the use of tin reagents as described by Stille, J. K., 1986, or through the use of boron reagents as described by Miyaura, N., et al., 1995.

(3)

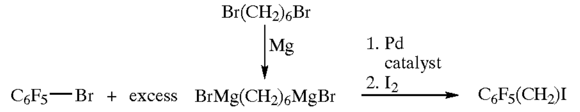

wherein $C_6F_5(CH_2)_6$ is $R^{C6ArF}$

The resultant alkyl iodide, $C_6F_5(CH_2)_6I$ abbreviated as $R^{C6ArF}I$, is reacted with Mg to form the Grignard reagent $R^{C6ArF}MgI$, which is then reacted with commercially available 2,6-dibromo-4-methylaniline, in a palladium-catalyzed coupling reaction, to produce the substituted aniline compound shown in the equation (4) below.

(4)

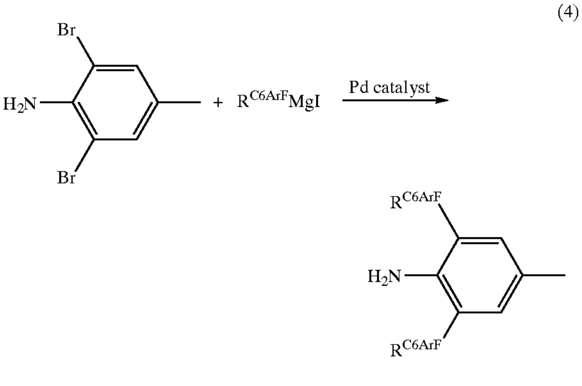

This substituted aniline is reacted with aqueous glyoxal, paraformaldehyde and hydrochloric acid according to procedures as described in U.S. Pat. No. 5,077,414, to A. J. Arduengo, III incorporated herein by reference to produce the substituted imidazolium cation shown below in formula X:

X

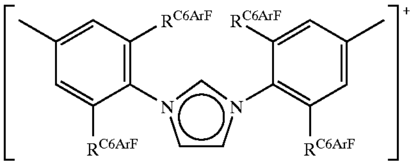

Deprotonation of this imidazolium cation using procedures as described in Arduengo, A. J. et al. 1999 produces the neutral N-heterocyclic carbene shown below and abbreviated as $Im^{ArC6ArF}$ as shown in formula XIII.

XIII

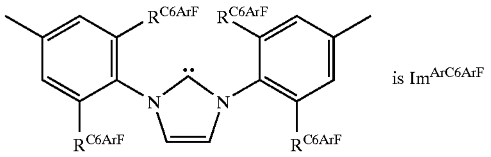

$Im^{ArC6ArF}$ is reacted with $CpW(CO)_2(PPh_3)H$ to produce $CpW(CO)_2(Im^{ArC6ArF})H$ using a procedure analogous to that described in Dioumaev, V. K., et al., 2003. Reaction of $CpW(CO)_2(Im^{ArC6ArF})H$ with $Ph_3C^+B(C_6F_5)_4^-$ produces $CpW(CO)_2(Im^{ArC6ArF})^+B(C_6F_5)_4^-$ by a procedure as described in Dioumaev V. K., et al., 2003.

Example 25

Synthesis of $(C_5H_5)W(CO)_2(PR^{C6ArF}{}_3)(Et_2C{=}O)^+B(C_6F_5)_4^-$

An excess amount (greater than 3 molar equivalents) of the Grignard reagent $R^{C6ArF}MgI$ as proposed in example A2 is reacted with either $PCl_3$ or $P(OPh)_3$ in diethyl ether for 6 hours to produce the trialkylphosphine $PR^{C6ArF}{}_3$. Then $PR^{C6ArF}{}_3$ is reacted with $CpW(CO)_3H$ to produce $(C_5H_5)W(CO)_2(PR^{C6ArF}{}_3)H$, using a procedure analogous to those described in: A. Bainbridge, A., et al. 1968. Hydride transfer from $(C_5H_5)W(CO)_2(PR^{C6ArF}{}_3)H$ to $Ph_3C^+B(C_6F_5)_4^-$ is carried out in the presence of $Et_2C{=}O$, using a procedure analogous to those described in Voges, M. H. and Bullock, R. M., 2002 to form $(C_5H_5)W(CO)_2W(PR^{C6ArF}{}_3)(Et_2C{=}O)^+B(C_6F_5)_4^-$ having the structure XIV shown below.

XIV

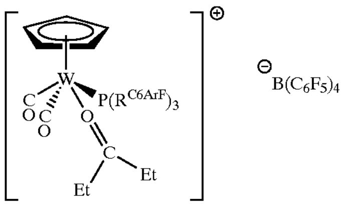

Example 26

Synthesis of the Ir Catalyst $(1,5\text{-cyclooctadiene})Ir[PCy_3](pyridine)^+PF_6^-$ is prepared following a synthetic procedure described in Stork, G., Kahne, D. E., 1983 and is thereafter reacted with $PR^{C6ArF}{}_3$ prepared as described above in example 25 at room temperature in $CH_2Cl_2$ for 10 minutes to produce $[(1,5\text{-cyclooctadiene})Ir(PR^{C6ArF}{}_3)(pyridine)]^+PF_6^-$.

Example 27

Catalytic Hydrosilyation of a Ketone

In a glove box, a complex of $[(1,3\text{-}(C_6F_5C_6H_{12})_2C_5H_3]W(CO)_2IMes)^+B(C_6F_5)^-{}_4$ as prepared in Example 23 and (5 mg), 3-pentanone (160 μL), and $HSiEt_3$ (288 μL) are placed in an NMR tube equipped with a teflon valve. Two sealed capillaries with $C_6D_6$ are placed in the same tube for NMR lock purpose. The tube is shaken to mix the ingredients. The reaction can be carried out at room temperature (about 23° C.) or at elevated temperatures from about 30° C. to about 150° C. The progress of the reaction is periodically monitored by $^1H$ NMR. After 2 hours at room temperature, a high conversion to alkoxysilane ($Et_2CHOSiEt_3$) is observed. The catalyst is separated from the product by decanting the liquid product from the catalyst. The solid catalyst can be reused without any loss of activity or selectivity. In cases where the catalyst is partially miscible with the product solution, cooling the reaction mixture from about 0° C. to about −78° C. results in the precipitation of most of catalyst at the end of the reaction.

Example 28

Catalytic Hydrosilyation of a Ketone

In a glove box, a complex of $(C_5H_5)W(CO)_2(Im^{ArC6ArF})^+B(C_6F_5)_4^-)$ as prepared in Example 24 and (5 mg), 3-pentanone (160 μL), and $HSiEt_3$ (288 μL) are placed in an NMR tube equipped with a teflon valve. Two sealed capillaries with $C_6D_6$ are placed in the same tube for NMR lock purpose. The tube is shaken to mix the ingredients. The reaction can be carried out at room temperature (about 23° C.) or at elevated temperatures from about 30° C. to about 150° C. (please complete) The progress of the reaction is periodically monitored by $^1H$ NMR. After 2 hours at room temperature, a high conversion to alkoxysilane ($Et_2CHOSiEt_3$) is observed. The catalyst is separated from the product by decanting the liquid product from the catalyst. The solid catalyst can be reused without any loss of activity or selectivity. In cases where the catalyst is partially miscible with the product solution, cooling the reaction mixture from about 0° C. to about −78° C. results in the precipitation of most of catalyst at the end of the reaction.

Example 29

Catalytic Hydrosilyation of a Ketone

In a glove box, a complex of $(C_6H_5)W(CO)_2(PR^{C6ArF}{}_3)(Et_2C{=}O)^+B(C_6F_5)_4^-$ as prepared in Example 25 (please complete) and (5 mg), 3-pentanone (160 μL), and $HSiEt_3$ (288 μL) are placed in an NMR tube equipped with a teflon valve. Two sealed capillaries with $C_6D_6$ are placed in the same tube for NMR lock purpose. The tube is shaken to mix the ingredients. The reaction can be carried out at room temperature (about 23° C.) or at elevated temperatures from about 30° C. to about 150° C. The progress of the reaction is periodically monitored by $^1H$ NMR. After 2 hours at room temperature, a high conversion to alkoxysilane ($Et_2CHOSiEt_3$) is observed. The catalyst is separated from the product by decanting the liquid product from the catalyst. The solid catalyst can be reused without any loss of activity or selectivity. In cases where the catalyst is partially miscible with the product solution, cooling the reaction mixture from about 0° C. to about −78° C. results in the precipitation of most of catalyst at the end of the reaction.

Example 30

Catalytic Hydrogenation of a Ketone

In a glove box a complex of $[(1,3\text{-}(C_6F_5C_6H_{12})_2C_5H_3]W(CO)_2(IMes)^+B(C_6F_5)_4^-$ as prepared in Example 23 (5 mg), and 3-pentanone (160 $\mu$L, 5.65 mmol), are placed in a glass tube (125 mL capacity) equipped with a teflon value. The solution is freeze-pump-thawed, frozen again, and the entire tube is submersed in liquid nitrogen. The tube is then filled with about 1.1 atm $H_2$, sealed, and warmed to room temperature. The reaction is carried out at 50° C. in a constant-temperature bath. After 7 days a substantial conversion of the 3-pentanone is hydrogenated to produce, 3-pentanol, an exclusive. Cooling the reaction mixture from about 0° C. to about −78° C. results in the precipitation of the catalyst at the end of the reaction. The solid catalyst can be reused without any loss of activity or selectivity.

Example 31

Catalytic Hydrogenation of a Ketone

In a glove box a complex of $(C_5H_5)W(CO)_2(Im^{ArC6ArF})^+ B(C_6F_5)_4^-)$ as prepared in Example 24 (5 mg), and 3-pentanone (160 $\mu$L, 5.65 mmol), are placed in a glass tube (125 mL capacity) equipped with a teflon value. The solution is freeze-pump-thawed, frozen again, and the entire tube is submersed in liquid nitrogen. The tube is then filled with about 1.1 atm $H_2$, sealed, and warmed to room temperature. The reaction is carried out at 50° C. in a constant-temperature bath. After 7 days a substantial conversion of the 3-pentanone is hydrogenated to produce, 3-pentanol, an exclusive. Cooling the reaction mixture from about 0° C. to about −78° C. results in the precipitation of the catalyst at the end of the reaction. The solid catalyst can be reused without any loss of activity or selectivity.

Example 32

Catalytic Hydrogenation of a Ketone

In a glove box a complex of $(C_6H_5)W(CO)_2(PR^{C6ArF}{}_3)(Et_2C{=}O)^+B(C_6F_5)_4^-$ as prepared in Example 25 (5 mg), and 3-pentanone (160 $\mu$L, 5.65 mmol), are placed in a glass tube (125 mL capacity) equipped with a teflon value. The solution is freeze-pump-thawed, frozen again, and the entire tube is submersed in liquid nitrogen. The tube is then filled with about 1.1 atm $H_2$, sealed, and warmed to room temperature. The reaction is carried out at 50° C. in a constant-temperature bath. After 7 days a substantial conversion of the 3-pentanone is hydrogenated to produce, 3-pentanol, an exclusive. Cooling the reaction mixture from about 0° C. to about −78° C. results in the precipitation of the catalyst at the end of the reaction. The solid catalyst can be reused without any loss of activity or selectivity.

Example 33

Catalytic Hydrogenation of a Ketone

In a glove box a complex of $(C_5H_5)W(CO)_2(Im^{ArC6ArF})^+ B(C_6F_5)_4^-$ as prepared in Example 24 (please confirm) (5 mg), and 3-pentanone (160 $\mu$L, 5.65 mmol), are placed in a glass tube (125 mL capacity) equipped with a teflon value. The solution is freeze-pump-thawed, frozen again, and the entire tube is submersed in liquid nitrogen. The tube is then filled with about 1.1 atm $H_2$, sealed, and warmed to room temperature. The reaction is carried out at 50° C. in a constant-temperature bath. After 7 days a substantial conversion of the 3-pentanone is hydrogenated to produce, 3-pentanol, an exclusive. Cooling the reaction mixture from about 0° C. to about −78° C. results in the precipitation of the catalyst at the end of the reaction. The solid catalyst can be reused without any loss of activity or selectivity.

Example 34

Catalytic Hydrogenation of Alkenes with an Iridium Catalyst 1,5-cyclooctadiene) $Ir[P(RAr^F)_3]$ (pyridine)$^+PF_6^-$ (2.0 mg) as prepared as in Example 26 $(CH_3)_2C{=}C(CH_3)_2$ (1.0 mL) is stirred under hydrogen (1 atmosphere) for 6 hours, resulting in the conversion of $(CH_3)_2C{=}C(CH_3)_2$ to the hydrogenation product, $(CH_3)_2CHCH(CH_3)_2$. The reaction solution is cooled from about 0° C. to about −78° C., resulting in the precipitation of most of the iridium catalyst. The catalyst is separated from the hydrogenation product by dicanting the liquid product from the catalyst. The catalyst can be reused without any loss of activity or selectivity.

BIBLIOGRAPHY

The following publications, mentioned in the foregoing specification, are incorporated herein by reference as if set forth in full for all they disclose:

Dioumaev, V. K., Szalda, D. J., Hanson, J., Franz, J. A. & Bullock, R. M., "An N-Heterocyclic Carbene as a Bidentate Hemilabile Ligand: A Synchrotron X-ray Diffraction and Density Functional Theory Study," *Chem. Commun.,* 1670, (2003).

Yang, Z. Y., Burton, D. J., *J. Fluorine Chem.,* 102, 89, (2000).

Venier, C. G., Casserly, E. W., *J. Am. Chem. Soc.,* 112, 2808, (1990).

Cheng, T. Y., Brunsehweig, B. S., Bullock, R. N., *J. Am Chem. Soc.,* 120, 13121, (1998).

Bainbridge, A., Craig, P. J. Green M., J. Chem Sec., (A), 2715, (1968).

Diederich, F., Stang, P. J., eds. *Metal-catalyzed Cross-coupling Reactions*, Wiley-VCH, Weinheim, (1998).

Hayashi, T., et al. in *J. Am. Chem. Soc.* 106, 158 (1984).

Stille, J. K., *Angew. Chem., Int. Ed. Engl.* 25, 508 (1986).

Miyaura, N., et al., *Chem. Rev.* 95, 2457 (1995).

Arduengo, A. J. et al., *Tetrahedron* 55, 14523 (1999).

Voges, M. H. and Bullock, R. M. in *J. Chem. Soc., Dalton Trans.* 759 (2002).

Stork, G.; Kahne, D. E., "Stereocontrol in Homogeneous Catalytic Hydrogenation via Hydroxyl Group Coordination," *J. Am. Chem. Soc.,* 105, 1072–1073 (1983).

Thus, while there have been described what are presently believed to be preferred embodiments of the present inventions, those skilled in the art will resolve that other and further modifications and changes can be made without departing from the true spirit of the invention, and it in intended to include all such changes and modifications as come within the scope of the invention and as pointed out in the appended claims.

What is claimed is:

1. An organometallic complex comprising:

a catalyst containing a transition metal, at least a ligand and a component having the formula $GAr^F$, wherein $Ar^F$ is an aromatic ring system selected from the group consisting of phenyl, naphthalenyl, anthracenyl, fluorenyl, and indenyl, said aromatic ring system having at least a substituent selected from the group consisting of fluorine, hydrogen, hydrocarbyl and fluorinated hydrocarbyl, G is substituted or unsubstituted $(CH_2)_n$ or $(CF_2)_n$, wherein n is from 1 to 30, wherein further one or more $CH_2$ or $CF_2$ groups are optionally replaced by NR, PR, $SiR_2$, BR, O or S, and R is hydrocarbyl or substituted hydrocarbyl, $GAr^F$ being covalently bonded to either said transition metal or said ligand of said catalyst, thereby rendering said cationic organometallic complex liquid.

2. The organometallic complex according to claim 1, wherein said catalyst is represented by formula I $$[CpM(CO)_2(NHC)L_k]^+A^- \quad \text{I}$$

wherein M is a metal selected from molybdenum or tungsten; Cp is substituted or unsubstituted cyclopentadienyl radical represented by the formula $[C_5Q^1Q^2Q^3Q^4Q^5]$, wherein $Q^1$ to $Q^5$ are independently selected from the group consisting of H radical, $GAr^F$, $C_{1-20}$ hydrocarbyl radical, substituted hydrocarbyl radical, hydrocarbyl radical substituted by $GAr^F$, halogen radical, halogen-substituted hydrocarbyl radical, —OR, —C(O)R', —$CO_2$R', —$SiR'_3$, —NR'R" wherein R' and R" are independently selected from the group consisting of H radical, $GAr^F$, $C_{1-20}$ hydrocarbyl radical, halogen radical, and halogen-substituted hydrocarbyl radical, wherein said $Q^1$ to $Q^5$ radicals can be optionally linked to each other to form a stable bridging group; NHC is any N-heterocyclic carbene ligand, L is either any neutral ligand, wherein k is a number from 0 to 1 or L is an anionic ligand wherein k is 2, and $A^-$ is an anion.

3. The organometallic complex according to claim 2, wherein NHC is an unsubstituted or substituted N-heterocyclic carbene ligand selected from the group consisting of carbenes represented by formula III

III

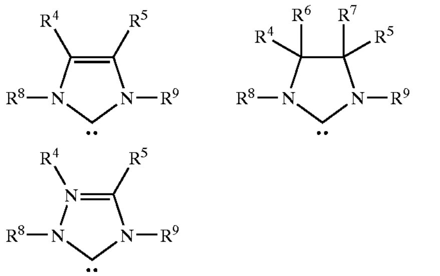

wherein $R^4$, $R^5$, $R^6$, $R^7$, $R^8$ and $R^9$ are each independently hydrogen, $GAr^F$, halogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthiol, aryl thiol, $C_1$–$C_{20}$ alkylsulfonyl and $C_1$–$C_{20}$ alkylsulfinyl, wherein further each $R^4$, $R^5$, $R^6$, $R^7$, $R^8$ and $R^9$ is optionally substituted with one or more moieties selected from the group consisting of $C_1$–$C_{20}$ hydrocarbyl, hydrocarbyl radical substituted by $GAr^F$, $C_1$–$C_{20}$ alkoxy, hydroxyl, thiol, thioether, ketone, aldehyde, ester, ether, amine, imine, amide, nitro, carboxylic acid, disulfide, carbonate, isocyanate, carbodiimide, carboalkoxy, carbamate and halogen, wherein $R^4$, $R^5$, $R^6$, $R^7$, $R^8$ and $R^9$ radicals are optionally linked to each other to form a stable bridging group.

4. The organometallic complex according to claim 2, wherein L is selected from the group consisting of a hydrocarbon or halogenated hydrocarbon molecule, a dihydrogen ($H_2$) or hydrosilane, a ketone, an aldehyde or an ester, an alkoxysilane, ether or alcohol molecule, a combination of two anionic ligands selected from the group consisting of hydride ($H^-$), silyl $(SiR^{10}R^{11}R^{12})^-$ and mixtures thereof, wherein $R^{10}$, $R^{11}$, $R^{12}$ are independently hydrogen, halogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthiol, aryl thiol, $C_1$–$C_{20}$ alkylsulfonyl and $C_1$–$C_{20}$ alkylsulfinyl, wherein further each $R^{10}$, $R^{11}$, $R^{12}$ is optionally substituted with one or more moieties selected from the group consisting of $C_1$–$C_{20}$ hydrocarbyl, $C_1$–$C_{20}$ alkoxy, hydroxyl, thiol, thioether, ketone, aldehyde, ester, ether, amine, imine, amide, nitro, carboxylic acid, disulfide, carbonate, isocyanate, carbodiimide, carboalkoxy, carbamate and halogen.

5. The organometallic complex according to claim 1, wherein said anion ($A^-$) is selected from the group consisting of $BF_4^-$, $PF_6^-$, $SbF_6^-$, $CF_3SO_3^-$, $CB_{11}H_{12}^-$, $CB_9H_{10}^-$ $CB_9H_5X_5^-$, $CB_{11}H_6X_6^-$, wherein X is F Cl, Br or I, $HBR_3^-$, wherein R is a hydrocarbyl or substituted hydrocarbyl, and $[(M')Z^1Z^2 \ldots Z^n]^-$, M' is an element selected from atoms of group 13, n is the total number of Z ligands or n is 4, and $Z^1$ to $Z^n$ are independently selected from the group consisting of H radical, $GAr^F$, $C_{1-20}$ hydrocarbyl radical, substituted hydrocarbyl radical, hydrocarbyl radicals substituted by $GAr^F$, halogens, halogen-substituted hydrocarbyl radical, hydrocarbyl-, halogen-substituted hydrocarbyl organometalloid radical, —OR, —C(O)R', —$CO_2$R', and —NR'R", wherein R' and R" are independently selected from the group consisting of H radicals, $C_{1-20}$ hydrocarbyl radicals, halogens, and halogen-substituted hydrocarbyl radical; said $Z^1$ to $Z^n$ radicals optionally linked to each other to form a stable bridging group.

6. The organometallic complex according to claim 5, wherein said catalyst is selected from the group consisting of (1,5-cyclooctodiene)Ir($PR^{C6ArF}_3$)(pyridine)$^+PF_6^-$, $(C_5H_5)$W $(CO)_2(PR^{C6ArF}_3)(Et_2C{=}O)^+B(C_6F_5)_4^-$, and $(C_5H_5)$W $(CO)_2$ $(Im^{ArC6ArF})^+B(C_6F_5)_4^-$, wherein $R^{C6ArF}$ is $C_6F_5(CH_2)_6$, and $Im^{ArC6ArF}$ is represented by formula X

X

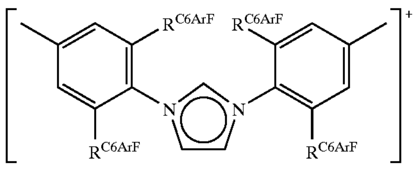

.

7. The organometallic complex according to claim 1, wherein said catalytic reaction is solvent-free.

8. The organometallic complex according to claim 1, wherein said cationic organometallic complex is a stable liquid clathrate.

9. The organometallic complex according to claim 1, wherein said catalyst is represented by the formula XI $$[CpM(CO)_2(PQ^6Q^7Q^8)L_k]^+A^- \quad \text{XI}$$

wherein M is a molybdenum or tungsten atom; Cp is substituted or unsubstituted cyclopentadienyl radical represented by the formula $[C_5Q^1Q^2Q^3Q^4Q^5]$, wherein $Q^1$ to $Q^5$ are independently selected from the group consisting of H radical, $GAr^F$, $C_{1-20}$ hydrocarbyl radical substituted hydrocarbyl radical, including hydrocarbyl radicals substituted by $GAr^F$, halogen radical, halogen substituted hydrocarbyl radical, —OR, —C(O)R', —$CO_2$R', —$SiR'_3$, —NR'R" wherein R' and R" are independently selected from the group consisting of H radical, $C_{1-20}$ hydrocarbyl radical, halogen radical, and halogen-substituted hydrocarbyl radical, wherein said $Q^1$ to $Q^5$ radicals can be optionally linked to each other to form a stable bridging group; $PQ^6Q^7Q^8$ is a phosphine ligand, wherein $Q^6$, $Q^7$, $Q^8$ represent three groups independently selected from the group consisting of H radical, $GAr^F$, $C_{1-20}$ hydrocarbyl radical substituted hydrocarbyl radical, including hydrocarbyl radicals substituted by $GAr^F$, halogen radical, halogen substituted hydrocarbyl radical, —OR, —C(O)R', —$CO_2$R', —$SiR'_3$, —NR'R" wherein R' and R" are independently selected from the group consisting of H radical, $C_{1-20}$ hydrocarbyl radical, halogen radical, and halogen-substituted hydrocarbyl radical, wherein all three $Q^6$, $Q^7$, $Q^8$ groups can be the same or different or two of the three groups can be the same; L is either any neutral ligand, wherein k is a number from 0 to 1 or L is an anionic ligand wherein k is 2, and $A^-$ is an anion.

10. The organometallic complex according to claim 9, wherein L is selected from the group consisting of a hydrocarbon or halogenated hydrocarbon molecule, a dihydrogen ($H_2$) or hydrosilane, a ketone, an aldehyde or an ester, an alkoxysilane, ether or alcohol molecule, a combination of two anionic ligands selected from the group consisting of hydride ($H^-$), silyl $(SiR^{10}R^{11}R^{12})^-$ and mixtures thereof, wherein $R^{10}$, $R^{11}$, $R^{12}$ are independently hydrogen, halogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthiol, aryl thiol, $C_1$–$C_{20}$ alkylsulfonyl and $C_1$–$C_{20}$ alkylsulfinyl, wherein further each $R^{10}$, $R^{11}$, $R^{12}$ is optionally substituted with one or more moieties selected from the group consisting of $C_1$–$C_{20}$ hydrocarbyl, $C_1$–$C_{20}$ alkoxy, hydroxyl, thiol, thioether, ketone, aldehyde, ester, ether, amine, imine, amide, nitro, carboxylic acid, disulfide, carbonate, isocyanate, carbodiimide, carboalkoxy, carbamate and halogen; wherein further the anion $A^-$ is selected from the group consisting of $BF_4^-$, $PF_6^-$, $SbF_6^-$, $CF_3SO_3^-$, $CB_{11}H_{12}^-$, $CB_9H_{10}^-CB_9H_5X_5^-$, $CB_{11}H_6X_6^-$, wherein X is F Cl, Br or I, $HBR_3^-$, wherein R is a hydrocarbyl or substituted hydrocarbyl, and $[(M')Z^1Z^2 \ldots Z^n]^-$, M' is an element selected from atoms of group 13, n is the total number of Z ligands or n is 4, and $Z^1$ to $Z^n$ are independently selected from the group consisting of H radical, $GAr^F$, $C_{1-20}$ hydrocarbyl radical, substituted hydrocarbyl radical, hydrocarbyl radicals substituted by $GAr^F$, halogens, halogen-substituted hydrocarbyl radical, hydrocarbyl-, halogen-substituted hydrocarbyl organometalloid radical, —OR, —C(O)R', —$CO_2$R', and —NR'R", wherein R' and R" are independently selected from the group consisting of H radicals, $C_{1-20}$ hydrocarbyl radicals, halogens, and halogen-substituted hydrocarbyl radical; said $Z^1$ to $Z^n$ radicals optionally linked to each other to form a stable bridging group.

11. A process for conducting a catalytic reaction, said process comprising:

contacting a reaction mixture including reactants with an organometallic complex comprising a catalyst containing a transition metal, at least a ligand and a component having the formula $GAr^F$, wherein $Ar^F$ is an aromatic ring system selected from the group consisting of phenyl, naphthalenyl, anthracenyl, fluorenyl and indenyl, said aromatic ring system having at least a substituent selected from the group consisting of fluorine, hydrogen, hydrocarbyl and fluorinated hydrocarbyl, G is substituted or unsubstituted $(CH_2)_n$ or $(CF_2)_n$, wherein n is from 1 to 30, wherein further one or more $CH_2$ or $CF_2$ groups are optionally replaced by NR, PR, $SiR_2$, BR, O or S, and R is hydrocarbyl or substituted hydrocarbyl, $GAr^F$ being covalently bonded to either said transition metal or said ligand of said catalyst, thereby rendering said cationic organometallic complex liquid;

recovering said catalyst after products have formed.

12. The process according to claim 11, wherein said catalyst is represented by formula I $$[CpM(CO)_2(NHC)L_k]^+A^- \qquad I$$

wherein M is a metal selected from molybdenum or tungsten; Cp is substituted or unsubstituted cyclopentadienyl radical represented by the formula $[C_5Q^1Q^2Q^3Q^4Q^5]$, wherein $Q^1$ to $Q^5$ are independently selected from the group consisting of H radical, $GAr^F$, $C_{1-20}$ hydrocarbyl radical, substituted hydrocarbyl radical, hydrocarbyl radical substituted by $GAr^F$, halogen radical, halogen-substituted hydrocarbyl radical, —OR, —C(O)R', —$CO_2$R', —$SiR'_3$, —NR'R" wherein R' and R" are independently selected from the group consisting of H radical, $GAr^F$, $C_{1-20}$ hydrocarbyl radical, halogen radical, and halogen-substituted hydrocarbyl radical, wherein said $Q^1$ to $Q^5$ radicals can be optionally linked to each other to form a stable bridging group; NHC is any N-heterocyclic carbene ligand, L is either any neutral ligand, wherein k is a number from 0 to 1 or L is an anionic ligand wherein k is 2, and $A^-$ is an anion.

13. The process according to claim 11, wherein NHC is an unsubstituted or substituted N-heterocyclic carbene selected from the group consisting of carbenes represented by formula III

III

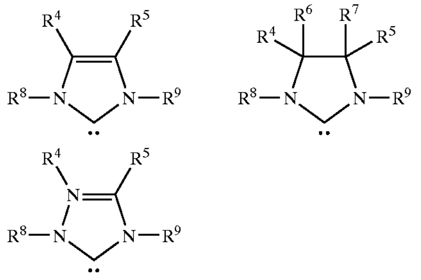

wherein $R^4$, $R^5$, $R^6$, $R^7$, $R^8$ and $R^9$ are each independently hydrogen, $GAr^F$, halogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthiol, aryl thiol, $C_1$–$C_{20}$ alkylsulfonyl and $C_1$–$C_{20}$ alkylsulfinyl, wherein further each $R^4$, $R^5$, $R^6$, $R^7$, $R^8$ and $R^9$ is optionally substituted with one or more moieties selected from the group consisting of $C_1$–$C_{20}$ hydrocarbyl, hydrocarbyl radical substituted by $GAr^F$, $C_1$–$C_{20}$ alkoxy, hydroxyl, thiol, thioether, ketone, aldehyde, ester, ether, amine, imine, amide, nitro, carboxylic acid, disulfide, carbonate, isocyanate, carbodiimide, carboalkoxy, carbamate and halogen, wherein $R^4$, $R^5$, $R^6$, $R^7$, $R^8$ and $R^9$ radicals are optionally linked to each other to form a stable bridging group.

14. The process according to claim 11, wherein L is selected from the group consisting of a hydrocarbon or halogenated hydrocarbon molecule, a dihydrogen ($H_2$) or hydrosilane, a ketone, an aldehyde or an ester, an alkoxysilane, ether or alcohol molecule, a combination of two anionic ligands selected from the group consisting of hydride ($H^-$), silyl $(SiR^{10}R^{11}R^{12})^-$ and mixtures thereof, wherein $R^{10}$, $R^{11}$, $R^{12}$ are independently hydrogen, halogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthiol, aryl thiol, $C_1$–$C_{20}$ alkylsulfonyl and $C_1$–$C_{20}$ alkylsulfinyl, wherein further each $R^{10}$, $R^{11}$, $R^{12}$ is optionally substituted with one or more moieties selected from the group consisting of $C_1$–$C_{20}$ hydrocarbyl, $C_1$–$C_{20}$ alkoxy, hydroxyl, thiol, thioether, ketone, aldehyde, ester, ether, amine, imine, amide, nitro, carboxylic acid, disulfide, carbonate, isocyanate, carbodiimide, carboalkoxy, carbamate and halogen.

15. The process according to claim 11, wherein said anion ($A^-$) is selected from the group consisting of $BF_4^-$, $PF_6^-$, $SbF_6^-$, $CF_3SO_3^-$, $CB_{11}H_{12}^-$, $CB_9H_{10}^-CB_9H_5X_5^-$, $CB_{11}H_6X_6^-$, wherein X is F Cl, Br or I, $HBR_3^-$, wherein R is a hydrocarbyl or substituted hydrocarbyl, and $[(M')Z^1Z^2 \ldots Z^n]$, M' is an element selected from atoms of group 13, n is the total number of Z ligands or n is 4, and $Z^1$ to $Z^n$ are independently selected from the group consisting of H radical, $GAr^F$, $C_{1\text{-}20}$ hydrocarbyl radical, substituted hydrocarbyl radical, hydrocarbyl radicals substituted by $GAr^F$, halogens, halogen-substituted hydrocarbyl radical, hydrocarbyl-, halogen-substituted hydrocarbyl organometalloid radical, —OR, —C(O)R', —$CO_2$R', and —NR'R", wherein R' and R" are independently selected from the group consisting of H radicals, $C_{1\text{-}20}$ hydrocarbyl radicals, halogens, and halogen-substituted hydrocarbyl radical; said $Z^1$ to $Z^n$ radicals optionally linked to each other to form a stable bridging group.

16. The process according to claim 11, wherein said catalyst is selected from the group consisting of (1,5-cyclooctodiene)Ir($PR^{C6ArF}_3$)(pyridine)$^+PF_6^-$, $(C_5H_5)$W$(CO)_2$W($PR^{C6ArF}_3$)($Et_2C{=}O$)$^+B(C_6F_5)_4^-$, and $(C_5H_5)$W$(CO)_2$W($Im^{ArC6ArF}$)$^+B(C_6F_5)_4^-$, wherein $R^{C6ArF}$ is $C_6F_5(CH_2)_6$, and $Im^{ArC6ArF}$ is represented by formula X

X

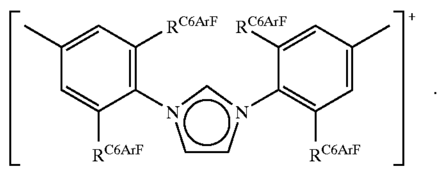

17. The process according to claim 11, wherein said catalytic reaction is solvent-free.

18. The process according to claim 17, wherein said solvent-free catalytic reaction is selected from the group consisting of hydrogenation of an organic compound, and hydrosilylation of an organic compound, wherein said organic compound contains at least one reducible functional group selected from the group consisting of R(C═O)$R^1$, R(C═O)H, and R($CO_2$)$R^1$, wherein R and $R^1$ are each independently selected from H, $C_{1\text{-}30}$ hydrocarbyl radicals or substituted hydrocarbyl radicals.

19. The process according to claim 11, wherein said contacting occurs at a temperature from about 20° C. to about 150° C.

20. The process according to claim 11, further comprising cooling the reaction mixture from about 0° C. to about −78° C.

21. The process according to claim 11, wherein said catalyst is represented by formula XI $$[CpM(CO)_2(PQ^6Q^7Q^8)L_k]^+A^- \qquad \text{XI}$$

wherein M is a molybdenum or tungsten atom; Cp is substituted or unsubstituted cyclopentadienyl radical represented by the formula $[C_5Q^1Q^2Q^3Q^4Q^5]$, wherein $Q^1$ to $Q^5$ are independently selected from the group consisting of H radical, $GAr^F$, $C_{1\text{-}20}$ hydrocarbyl radical substituted hydrocarbyl radical, including hydrocarbyl radicals substituted by $GAr^F$, halogen radical, halogen substituted hydrocarbyl radical, —OR, —C(O)R', —$CO_2$R', —$SiR'_3$, —NR'R" wherein R' and R" are independently selected from the group consisting of H radical, $C_{1\text{-}20}$ hydrocarbyl radical, halogen radical, and halogen-substituted hydrocarbyl radical, wherein said $Q^1$ to $Q^5$ radicals can be optionally linked to each other to form a stable bridging group; $PQ^6Q^7Q^8$ is a phosphine ligand, wherein $Q^6$, $Q^7$, $Q^8$ represent three groups independently selected from the group consisting of H radical, $GAr^F$, $C_{1\text{-}20}$ hydrocarbyl radical substituted hydrocarbyl radical, including hydrocarbyl radicals substituted by $GAr^F$, halogen radical, halogen substituted hydrocarbyl radical, —OR, —C(O)R', —$CO_2$R', —$SiR'_3$, —NR'R" wherein R' and R" are independently selected from the group consisting of H radical, $C_{1\text{-}20}$ hydrocarbyl radical, halogen radical, and halogen-substituted hydrocarbyl radical, wherein all three $Q^6$, $Q^7$, $Q^8$ groups can be the same or different or two of the three groups can be the same; L is either any neutral ligand, wherein k is a number from 0 to 1 or L is an anionic ligand wherein k is 2, and $A^-$ is an anion.

22. The organometallic complex according to claim 21, wherein L is selected from the group consisting of a hydrocarbon or halogenated hydrocarbon molecule, a dihydrogen ($H_2$) or hydrosilane, a ketone, an aldehyde or an ester, an alkoxysilane, ether or alcohol molecule, a combination of two anionic ligands selected from the group consisting of hydride ($H^-$), silyl $(SiR^{10}R^{11}R^{12})^-$ and mixtures thereof, wherein $R^{10}$, $R^{11}$, $R^{12}$ are independently hydrogen, halogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthiol, aryl thiol, $C_1$–$C_{20}$ alkylsulfonyl and $C_1$–$C_{20}$ alkylsulfinyl, wherein further each $R^{10}$, $R^{11}$, $R^{12}$ is optionally substituted with one or more moieties selected from the group consisting of $C_1$–$C_{20}$ hydrocarbyl, $C_1$–$C_{20}$ alkoxy, hydroxyl, thiol, thioether, ketone, aldehyde, ester, ether, amine, imine, amide, nitro, carboxylic acid, disulfide, carbonate, isocyanate, carbodiimide, carboalkoxy, carbamate and halogen; wherein further the anion $A^-$ is selected from the group consisting of $BF_4^-$, $PF_6^-$, $SbF_6^-$, $CF_3SO_3^-$, $CB_{11}H_{12}^-$, $CB_9H_{10}^-CB_9H_5X_5^-$, $CB_{11}H_6X_6^-$, wherein X is F Cl, Br or I, $HBR_3^-$, wherein R is a hydrocarbyl or substituted hydrocarbyl, and $[(M')Z^1Z^2 \ldots Z^n]^-$, M' is an element selected from atoms of group 13, n is the total number of Z ligands or n is 4, and $Z^1$ to $Z^n$ are independently selected from the group consisting of H radical, $GAr^F$, $C_{1\text{-}20}$ hydrocarbyl radical, substituted hydrocarbyl radical, hydrocarbyl radicals substituted by $GAr^F$, halogens, halogen-substituted hydrocarbyl radical, hydrocarbyl-, halogen-substituted hydrocarbyl organometalloid radical, —OR, —C(O)R', —$CO_2$R', and —NR'R", wherein R' and R" are independently selected from the group consisting of H radicals, $C_{1\text{-}20}$ hydrocarbyl radicals, halogens, and halogen-substituted hydrocarbyl radical; said $Z^1$ to $Z^n$ radicals optionally linked to each other to form a stable bridging group.

23. A method of preparing an organometallic complex including a catalyst containing a transition metal, a ligand and a component $GAr^F$ wherein $Ar^F$ is an aromatic ring system selected from the group consisting of phenyl, naphthalenyl, anthracenyl, fluorenyl and indenyl, said aromatic ring system having at least a substituent selected from the group consisting of fluorine, hydrogen, hydrocarbyl and fluorinated hydrocarbyl, G is substituted or unsubstituted $(CH_2)_n$ or $(CF_2)_n$, wherein n is from 1 to 30, wherein further one or more $CH_2$ or $CF_2$ groups are optionally replaced by NR, PR, $SiR_2$, BR, O or S, and R is hydrocarbyl or substituted hydrocarbyl, $GAr^F$ being covalently bonded to either said transition metal or said ligand of said catalyst, thereby rendering said cationic organometallic complex liquid, said method comprising:

(i) providing $GAr^F$, (ii) covalently bonding $GAr^F$ to either a metal or a ligand of said catalyst.

24. The method of claim 23, wherein said catalyst is of the formula I $$[CpM(CO)_2(NHC)L_k]^+A^- \qquad I$$

wherein M is a metal selected from molybdenum or tungsten; Cp is substituted or unsubstituted cyclopentadienyl radical represented by the formula $[C_5Q^1Q^2Q^3Q^4Q^5]$, wherein $Q^1$ to $Q^5$ are independently selected from the group consisting of H radical, $GAr^F$, $C_{1-20}$ hydrocarbyl radical, substituted hydrocarbyl radical, hydrocarbyl radical substituted by $GAr^F$, halogen radical, halogen-substituted hydrocarbyl radical, —OR, —C(O)R', —$CO_2R'$, —$SiR'_3$, —NR'R" wherein R' and R" are independently selected from the group consisting of H radical, $GAr^F$, $C_{1-20}$ hydrocarbyl radical, halogen radical, and halogen-substituted hydrocarbyl radical, wherein said $Q^1$ to $Q^5$ radicals can be optionally linked to each other to form a stable bridging group; NHC is any N-heterocyclic carbene ligand, L is either any neutral ligand, wherein k is a number from 0 to 1 or L is an anionic ligand wherein k is 2, and $A^-$ is an anion, wherein said catalyst is prepared by reacting a metal hydride represented by the formula II:

$$CpM(CO)_2(NHC)H \qquad II$$

with a hydride removing agent selected from $BR_3$ or a compound represented by formula $Y^+A^-$, wherein Y is selected from the group consisting of $(aryl)_3C^+$, $(aryl)_2HC^+$, $C_7H_7^+$, $R_3NH^+$, $Ag^+$ and $(C_5R_5)_2Fe^+$, wherein R is a hydrocarbyl or substituted hydrocarbyl, $A^-$ is selected from the group consisting of $BF_4^-$, $PF_6^-$, $SbF_6^-$, $CF_3SO_3^-$, $CB_{11}H_{12}^-$, $CB_9H_{10}^-CB_9H_5X_5^-$, $CB_{11}H_6X_6^-$, wherein X is F Cl, Br or I, $HBR_3^-$, wherein R is a hydrocarbyl or substituted hydrocarbyl, and $[(M')Z^1Z^2 \ldots Z^n]^-$, M' is an element selected from atoms of group 13, n is the total number of Z ligands or n is 4, and $Z^1$ to $Z^n$ are independently selected from the group consisting of H radical, $GAr^F$, $C_{1-20}$ hydrocarbyl radical, substituted hydrocarbyl radical, hydrocarbyl radicals substituted by $GAr^F$, halogens, halogen-substituted hydrocarbyl radical, hydrocarbyl-, halogen-substituted hydrocarbyl organometalloid radical, —OR, —C(O)R', —$CO_2R'$, and —NR'R", wherein R' and R" are independently selected from the group consisting of H radicals, $C_{1-20}$ hydrocarbyl radicals, halogens, and halogen-substituted hydrocarbyl radical; said $Z^1$ to $Z^n$ radicals optionally linked to each other to form a stable bridging group.

25. The method according to claim 24, wherein said metal hydride is prepared by reacting a phosphine hydride represented by the formula V $$CpM(CO)_2(PR_3)H \qquad V$$

wherein R is any $C_1$–$C_{20}$ hydrocarbyl group with said NHC.

26. The method according to claim 24, wherein NHC is an unsubstituted or substituted N-heterocyclic carbene ligand selected from the group consisting of carbenes represented by formula III

III

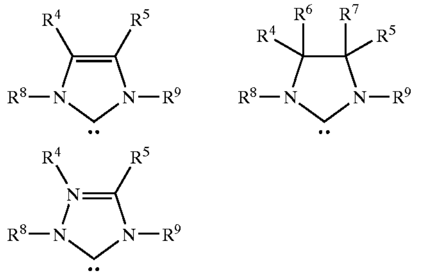

wherein $R^4$, $R^5$, $R^6$, $R^7$, $R^8$ and $R^9$ are each independently hydrogen, $GAr^F$, halogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthiol, aryl thiol, $C_1$–$C_{20}$ alkylsulfonyl and $C_1$–$C_{20}$ alkylsulfinyl, wherein further each $R^4$, $R^5$, $R^6$, $R^7$, $R^8$ and $R^9$ is optionally substituted with one or more moieties selected from the group consisting of $C_1$–$C_{20}$ hydrocarbyl, hydrocarbyl radical substituted by $GAr^F$, $C_1$–$C_{20}$ alkoxy, hydroxyl, thiol, thioether, ketone, aldehyde, ester, ether, amine, imine, amide, nitro, carboxylic acid, disulfide, carbonate, isocyanate, carbodiimide, carboalkoxy, carbamate and halogen, wherein $R^4$, $R^5$, $R^6$, $R^1$, $R^8$ and $R^9$ radicals are optionally linked to each other to form a stable bridging group.

27. The method according to claim 24, wherein L is selected from the group consisting of a hydrocarbon or halogenated hydrocarbon molecule, a dihydrogen ($H_2$) or hydrosilane, a ketone, an aldehyde or an ester, an alkoxysilane, ether or alcohol molecule, a combination of two anionic ligands selected from the group consisting of hydride ($H^-$), silyl $(SiR^{10}R^{11}R^{12})^-$ and mixtures thereof, wherein $R^{10}$, $R^{11}$, $R^{12}$ are independently hydrogen, halogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthiol, aryl thiol, $C_1$–$C_{20}$ alkylsulfonyl and $C_1$–$C_{20}$ alkylsulfinyl, wherein further each $R^{10}$, $R^{11}$, $R^{12}$ is optionally substituted with one or more moieties selected from the group consisting of $C_1$–$C_{20}$ hydrocarbyl, $C_1$–$C_{20}$ alkoxy, hydroxyl, thiol, thioether, ketone, aldehyde, ester, ether, amine, imine, amide, nitro, carboxylic acid, disulfide, carbonate, isocyanate, carbodiimide, carboalkoxy, carbamate and halogen.

28. The method according to claim 23, wherein said catalyst is of the formula XII $$[CpM(CO)_2(PQ^6Q^7Q^8)L_k]^+A^- \qquad XII$$

wherein M is a molybdenum or tungsten atom; Cp is substituted or unsubstituted cyclopentadienyl radical represented by the formula $[C_5Q^1Q^2Q^3Q^4Q^5]$, wherein $Q^1$ to $Q^5$ are independently selected from the group consisting of H radical, $GAr^F$, $C_{1-20}$ hydrocarbyl radical substituted hydrocarbyl radical, including hydrocarbyl radicals substituted by $GAr^F$, halogen radical, halogen substituted hydrocarbyl radical, —OR, —C(O)R', —$CO_2R'$, —$SiR'_3$, —NR'R" wherein R' and R" are independently selected from the group consisting of H radical, $C_{1-20}$ hydrocarbyl radical, halogen radical, and halogen-substituted hydrocarbyl radical, wherein said $Q^1$ to $Q^5$ radicals can be optionally linked to each other to form a stable bridging group; $PQ^6Q^7Q^8$ is a phosphine ligand, wherein $Q^6$, $Q^7$, $Q^8$ represent three groups independently selected from the group consisting of H radical, $GAr^F$, $C_{1-20}$ hydrocarbyl radical substituted hydrocarbyl radical, including hydrocarbyl radicals substituted by $GAr^F$, halogen radical, halogen substituted hydrocarbyl radical, —OR, —C(O)R', —$CO_2$R', —SiR'$_3$, —NR'R" wherein R' and R" are independently selected from the group consisting of H radical, $C_{1-20}$ hydrocarbyl radical, halogen radical, and halogen-substituted hydrocarbyl radical, wherein all three $Q^6$, $Q^7$, $Q^8$ groups can be the same or different or two of the three groups can be the same; L is either any neutral ligand, wherein k is a number from 0 to 1 or L is an anionic ligand wherein k is 2, and $A^-$ is an anion.

29. The organometallic complex of claim 28, wherein L is selected from the group consisting of a hydrocarbon or halogenated hydrocarbon molecule, a dihydrogen ($H_2$) or hydrosilane, a ketone, an aldehyde or an ester, an alkoxysilane, ether or alcohol molecule, a combination of two anionic ligands selected from the group consisting of hydride ($H^-$), silyl $(SiR^{10}R^{11}R^{12})^-$ and mixtures thereof, wherein $R^{10}$, $R^{11}$, $R^{12}$ are independently hydrogen, halogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthiol, aryl thiol, $C_1$–$C_{20}$ alkylsulfonyl and $C_1$–$C_{20}$ alkylsulfinyl, wherein further each $R^{10}$, $R^{11}$, $R^{12}$ is optionally substituted with one or more moieties selected from the group consisting of $C_1$–$C_{20}$ hydrocarbyl, $C_1$–$C_{20}$ alkoxy, hydroxyl, thiol, thioether, ketone, aldehyde, ester, ether, amine, imine, amide, nitro, carboxylic acid, disulfide, carbonate, isocyanate, carbodiimide, carboalkoxy, carbamate and halogen; wherein further the anion $A^-$ is selected from the group consisting of $BF_4^-$, $PF_6^-$, $SbF_6^-$, $CF_3SO_3^-$, $CB_{11}H_{12}^-$, $CB_9H_{10}^-CB_9H_5X_5^-$, $CB_{11}H_6X_6^-$, wherein X is F Cl, Br or I, $HBR_3^-$, wherein R is a hydrocarbyl or substituted hydrocarbyl, and $[(M')Z^1Z^2 \ldots Z^n]^-$, M' is an element selected from atoms of group 13, n is the total number of Z ligands or n is 4, and $Z^1$ to $Z^n$ are independently selected from the group consisting of H radical, $GAr^F$, $C_{1-20}$ hydrocarbyl radical, substituted hydrocarbyl radical, hydrocarbyl radicals substituted by $GAr^F$, halogens, halogen-substituted hydrocarbyl radical, hydrocarbyl-, halogen-substituted hydrocarbyl organometalloid radical, —OR, —C(O)R', —$CO_2$R', and —NR'R", wherein R' and R" are independently selected from the group consisting of H radicals, $C_{1-20}$ hydrocarbyl radicals, halogens, and halogen-substituted hydrocarbyl radical; said $Z^1$ to $Z^n$ radicals optionally linked to each other to form a stable bridging group.

30. The method according to claim 23, wherein said catalyst is selected from the group consisting of (1,5-cyclooctodiene)Ir$(PR^{C6ArF}{}_3)$(pyridine)$^+PF_6^-$, $(C_5H_5)W(CO)_2(PR^{C6ArF}{}_3)(Et_2C{=}O)^+B(C_6F_5)_4^-$, and $(C_5H_5)W(CO)_2\ (Im^{ArC6ArF})^+B(C_6F_5)_4^-$, wherein $R^{C6ArF}$ is $C_6F_5(CH_2)_6$, and $Im^{ArC6ArF}$ is represented by formula X

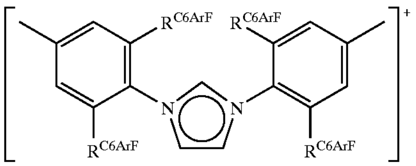

X

* * * * *